(12) United States Patent
Mueller et al.

(10) Patent No.: US 6,225,101 B1
(45) Date of Patent: May 1, 2001

(54) ISOLATED MYT1 POLYPEPTIDE

(75) Inventors: Paul R. Mueller, Chicago, IL (US); Thomas R. Coleman, Jenkintown, PA (US); Akiko Kumagai; William G. Dunphy, both of Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/337,386

(22) Filed: Jun. 21, 1999

Related U.S. Application Data

(62) Division of application No. 08/942,001, filed on Oct. 1, 1997, now Pat. No. 6,020,194.
(60) Provisional application No. 60/028,073, filed on Oct. 4, 1996.

(51) Int. Cl.[7] ............................... C12N 9/12; C07K 14/47
(52) U.S. Cl. ............................................ 435/194; 530/350
(58) Field of Search ............................. 530/350; 435/194

(56) References Cited

PUBLICATIONS

Berendsen, Science, vol. 282, pp. 642–643, Oct. 1998.*

* cited by examiner

*Primary Examiner*—Terry McKelvey
(74) *Attorney, Agent, or Firm*—Fish & Richardson P.C.

(57) ABSTRACT

The present invention provides a threonine/tyrosine kinase, Myt1, that phosphorylates the cyclin-dependent kinase, Cdc2, to provide regulation of the cell cycle at the G2/M interphase. Also included are polynucleotides encoding Myt1 polypeptide and antibodies that bind to Myt1. Methods of modulating Myt1 for preventing premature entry of the cell into mitosis or to accelerate entry into mitosis are also provided, as are methods for identifying agents that modulate Myt1.

6 Claims, 8 Drawing Sheets

FIG. 1A

(SEQUENCE ID NO: 2)

```
MPVPGDDMGETPLTRTPIPMPAYFSQAEQSFGLKKRGRSLCYTLPPRPPV        50
KSALPVSRIFPNKQRSWSQPRPQSVGFRSPQNKTPASKLYDQSKGDTFFK       100
QCFKSIXKLGRGSFGEVYKVQSLEDGCFTAVKRSVSPFRGESDRQRKLQE       150
VRKHERVGEHPMCLRFVRAWEEKRMLYLQTELCAGSLQQHSEEFAGSLPP       200
RRVWNITCDLLHGLKHLHDRNLLHLDIKPANVFISFSGVCKLGDFGLMVE       250
LDGTEGSGEAQEGDPRYMAPELLDGIFSKAADVFSLGMSLLEVACNMELP       300
KGGDGWQQLRQGHLPTEFTSDLPPDFLKVLSAMLEPDYRRRATVDWLLSL       350
PAIRNAERWRMVTLAQERTLGKIIAVYQFIWLLSFVFQWLNRPVIGFLH       400
YCGLRALPRSPPCSPFPNHLGESSFSSDWDDESLGDDVFEVPPSPLATHR       450
NLTYHGQELIGRHSPDLLSRPSLGSTSTPRNLSPEFSMRKRSALPTPNV        500
SRISQDSTGKRSTPSTSHSSSGFVDAEVQRTLFLPRNLLGMFDDATEQ        548
```

FIG. 1B (SEQUENCE ID NO: 8)
(SEQUENCE ID NO: 9)

FIG. 1D

DNA sequence of Xenopus Myt1 (SEQUENCE ID NO: 1)

```
   1 agtcatagaa gggactcggg gagtcggtgt gtgggaatgt gacggagatg cgcaaacggg
  61 cgggtgttgt tgaagaggcg ttggggggcg aaatccagaa ttgtccttct gtatatctgg
 121 agataaaaag gaccaccatt acgttcacct ttaaggtgcc tgctcattat gcctgttcca
 181 ggggatgaca tgggagagac tcccctgact cgcactccaa tccctatgcc tgcttacttt
 241 agccaggcag agcaaagctt ttcacttaag aaaagagggc gctctctttg ctatacccte
 301 ccacccagac ctccagttaa aagcgctcta cctgtaagcc gtatcttccc aaataaacag
 361 cgatcttgga gccagcccag accacagagc gtttctttte gaagtcccca aaataaaacc
 421 cctcgaagca agcttttatga ccagagcaaa ggagatacat ttttcaagca gtgttttaaa
 481 agcatttgca aattaggaag aggatccttt ggggaggtat acaaggtgca aagccttgag
 541 gatggatgct tctatgctgt aaagcgttct gtatctccgt tcgcggtga gtcagaccgg
 601 caacggaagc ttcaggaggt gaggaagcat gagcgagttg gggagcaccc caattgccta
 661 cgtttgtgc gagcagaaga agagaaacga atgctctacc ttcagacaga gttatgtgca
 721 gggagtttgc aacagcattc tgaagaattt gctggtctc ttcctccacg tcgagtatgg
 781 aacataactt gtgacctgct gcatggttctc aaacatcttc atgatcgcaa ccttctgcac
 841 cttgacatta agccagctaa tgtcttcatt tcttttttctg gtgtttgcaa acttggtgat
 901 ttcgactca tggtagaatt ggatgggact gaaggaagtg gggaagcaca ggaaggtgac
 961 cctcgctata tgcacctga actgtttggat ggtatctttt cgaaggctgc tgatgtgttc
1021 agtcttggaa tgagtcttct agaagtcgct tgcaatatgg agcttccgaa agcttggagat
1081 ggttggcaac agctgagaca agggcatctc cctacagagt ttacatcaga cctgccacca
1141 gattcctaa aagttctttc tgcaatgctg gagcctgatt accgcgccgg tgccacagta
1201 gactggctac tctcccttcc tgctatccgt aatgcagaga gatgcaggat ggtgacacta
1261 gcgcaggaaa ggacacttgg caagataata gcagtctatc agttcatagt ttggcttcta
1321 tctttcgtgt ttcaatggct aaatcgtcct gttataggat tttacatta ctgtggattg
1381 agggctcttc tcccttcacc ccctttctct ccttttccta accatcttgg ggagagcagc
1441 ttctctagtg caaggtcacc tgagagtctt ggtgatgatg tgtttgaggt accgccaagc
1501 ccactggcca ctcaccgaaa tctgacatac catgggcagg agctcattgg cagacattct
```

FIG. 1E

```
1561 ccagatctac tctcaaggcc gtcacttgga agtacctcta cccctcgcaa tttgtctcct
1621 gaattcagca tgagaaagag gtctgccctg cctctaacgc ctaatgtcag tcggattagc
1681 caggattcta caggcaagtc tagaagcccc tccaccagtc atagctcctc tggatttgtg
1741 gatgctgaag tccagcgtac cttattctt cctcgcaatc tgctcggtat gtttgacgat
1801 gccaccgagc aatgatagca gtgcagagta ccacacagca ccagacttt tatttta
1861 tcaggtgatc tttaacgcca accattggcc tatggcattg acctgtggc atatgaaagt
1921 gaaattgaga ggtctacaac atattggatg tattgagaca atggctattt atacaatgca
1981 cattcagctg tgaaaaatta cacccgatat ctgcatattc gcaaaagaaa atggatgttg
2041 tataaaaatg gtgactgggt tatggataat ataataggtg tgtttttcat gatatcgcca
2101 tgattaccgc taacatttct ataacttaag tttcagttc ttgtttaaag tgtgtgtgta
2161 tttatattta tataaaaaca ttttttttgg ga
```

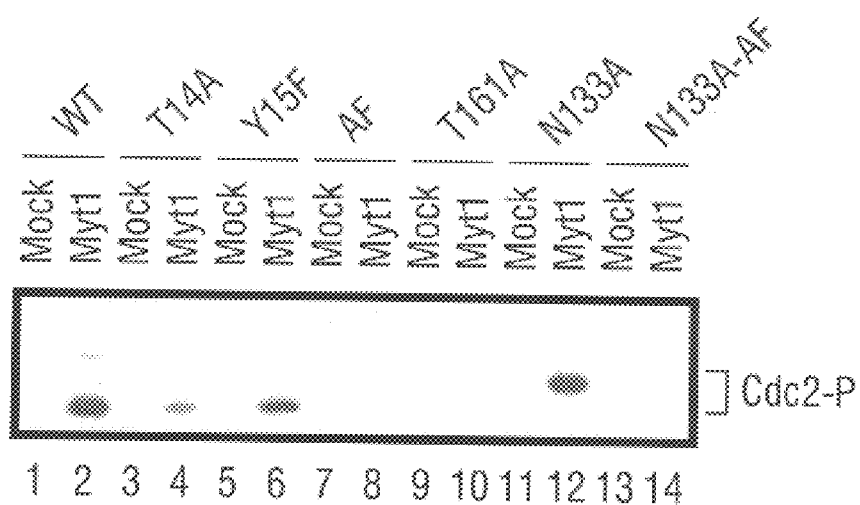
FIG. 2A
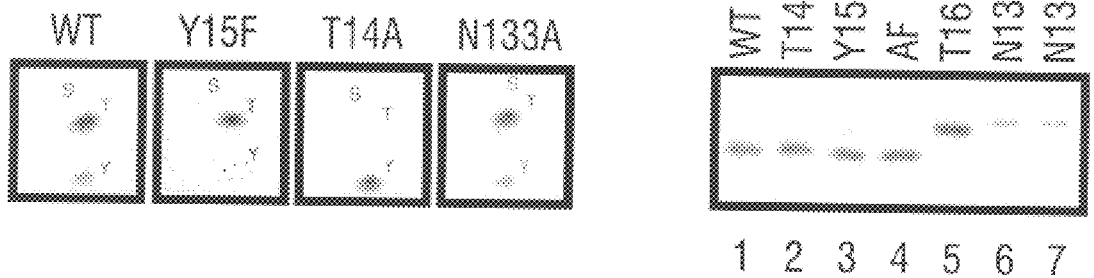
FIG. 2B
FIG. 2C

US 6,225,101 B1

ISOLATED MYT1 POLYPEPTIDE

This is a divisional of U.S. application Ser. No. 08/942,001, filed Oct. 1, 1997 now U.S. Pat. No. 6,020,194; and claims the benefit of priority under 35 USC §119(e) of U.S. provisional application Ser. No. 60/028,073, filed Oct. 4, 1996.

STATEMENT AS TO FEDERALLY SPONSORED RESEARCH

This invention was made in part with support from grant number GM 43974 from the National Institutes of Health. The government may have certain rights in this invention.

FIELD OF THE INVENTION

This invention relates generally to the cell cycle and mitosis. More specifically, the invention relates to a threonine and tyrosine protein kinase, Myt1, that is a Cdc2 inhibitory kinase regulated during the cell cycle in such a way that it plays a role in mitotic control.

BACKGROUND OF THE INVENTION

The replication cycle of a typical eukaryotic somatic cell consists of four phases: $G_1$, S (DNA synthesis), $G_2$, and M (mitosis). The result of this process is the generation of two daughter cells that are equivalent both in genetic makeup and in size to the original parental cell. Feedback controls operating at checkpoints ensure the faithful replication and segregation of the genetic material. In eukaryotic organisms, a general paradigm has emerged in which a family of proteins, called cyclins, and cyclin-dependent protein kinases (Cdks) regulate cell cycle progression. These mechanisms are at the level of reversible phosphorylation, binding to low-molecular-weight inhibitors, transcription, intracellular compartmentalization, and protein degradation.

The transition from $G_2$ to M phase requires the activity of M-phase-promoting factor (MPF), which is composed of Cdc2, an evolutionarily conserved serine/threonine-specific protein kinase, and B-type cyclins. The activity of Cdc2 is regulated not only by is association with B-type cyclins but also by reversible phosphorylation. Proper regulation of MPF ensures that mitosis occurs only after earlier phases of the cell cycle have been completed successfully. This strict control of MPF is largely post-translational, involving the phosphorylation of Cdc2 at three key residues. After Cdc2 associates with cyclin, the cyclin-dependent kinase (CDK)-activating kinase (CAK) phosphorylates Cdc2 on $Thr^{161}$. This phosphorylation would generate active MPF, but two additional phosphorylations on $Thr^{14}$ and $Tyr^{15}$ of Cdc2 suppress MPF activity during interphase. At the $G_2$-M transition, the Cdc25 protein dephosphorylates $Thr^{14}$ and $Tyr^{15}$, thereby allowing MPF to phosphorylate its mitotic substrates.

Phosphorylation on $Thr^{14}$ and $Tyr^{15}$ maintains Cdc2 in an inactive state throughout the S and $G_2$ phases of the cell cycle, and $Thr^{161}$ phosphorylation is required for the kinase activity of the complex. Dephosphorylation of both $Thr^{14}$ and $Tyr^{15}$ by the Cdc25 phosphatase in late $G_2$ activates Cdc2 and is an obligate step for the onset of mitosis. Exit from mitosis requires the proteolytic degradation of the B-type cyclins, which is mediated by ubiquitination.

Various genetic and biochemical studies have indicated that Wee1 is the kinase that phosphorylates Cdc2 on $Tyr^{15}$. Wee1 was originally identified in the fission yeast *Schizosaccharomyces pombe* as a critical negative regulator of mitosis. Subsequently, a second *S. pombe* homolog (Mik1) and Wee1 homologs from at least six other organisms have been found. In human and Xenopus, Wee1 is a soluble enzyme that phosphorylates Cdc2 on $Tyr^{15}$, but not on $Thr^{14}$.

SUMMARY OF THE INVENTION

The present invention is based on the discovery of a membrane-associated inhibitory kinase that phosphorylates Cdc2 on both $Thr^{14}$ and $Tyr^{15}$. Although Wee1 had been identified as the kinase that phosphorylates $Tyr^{15}$ in various organisms, the $Thr^{14}$-specific kinase had not been identified. A complementary DNA (cDNA) cloned from Xenopus, encodes Myt1 ("membrane-associated, tyrosine-and threonine-specific Cdc2 inhibitory kinase"). Myt1 is a membrane-associated protein that contains a putative transmembrane segment.

In a first embodiment, the invention provides a substantially purified Myt1 polypeptide exemplified by the amino acid sequence of SEQ ID NO:2 and polynucleotides encoding SEQ ID NO:2. Also included are vectors and host cells containing the polynucleotide encoding Myt1 of the invention.

In another embodiment, the invention provides a method of measuring the activity of Myt1 in a sample. The method includes incubating a test sample with a substrate for Myt1 and labeled phosphate under conditions sufficient to allow phosphorylation of the substrate; and determining the rate of incorporation of labeled phosphate into the substrate, wherein the rate of incorporation is a measure of Myt1 activity. The substrate is preferably Cdc2.

In yet another embodiment, the invention provides a method for measuring the synthesis of Myt1 in a test sample. The method includes a) obtaining a biological sample; b) contacting the sample with an antibody that specifically binds an Myt1 polypeptide of the invention; and c) detecting the antibody bound to Myt1 polypeptide, wherein the level of Myt1 synthesis is determined by the amount of bound antibody. Preferably the antibody is an Myt1-specific monoclonal antibody.

In another embodiment, the invention provides a method for measuring the level of expression of Myt1 in a test sample. The method includes a) isolating total or polyadenylated RNA from the test sample; b) incubating the RNA with a polynucleotide probe specific for an Myt1 polynucleotide of the invention; and c) determining the amount of the probe hybridized to the RNA, wherein the level of expression of Myt1 is directly related to the amount of Myt1 probe hybridized to the RNA.

In another embodiment, the invention provides a method for identifying a reagent that modulates Myt1 activity. The method includes a) obtaining a test sample containing Myt1; b) incubating the test sample with a substrate for the Myt1 polypeptide of the invention, the reagent, and labeled phosphate under conditions sufficient to allow phosphorylation of the substrate in the absence of the reagent; c) detecting phosphorylation of the substrate; and d) comparing the effect of the reagent on Myt1 activity relative to a control not containing the reagent, wherein any variation compared to control is indicative of a reagent which modulates Myt1 substrate phosphorylation. Preferably, the substrate is Cdc2. The modulation measured may be either inhibition of Myt1 activity or stimulation of Myt1 activity.

In another embodiment, the invention provides a method for identifying a reagent that modulates Myt1 synthesis. The method includes a) providing a sample capable of Myt1 synthesis; b) incubating the sample with a reagent under conditions that allow synthesis of Myt1 in the absence of the reagent; c) detecting an Myt1 polypeptide of the invention; and d) comparing the effect of the reagent on Myt1 synthesis relative to a control not containing the reagent, wherein any variation compared to control is indicative of a reagent which modulates Myt1 synthesis.

In another embodiment, the invention provides a method for identifying a reagent that modulates Myt1 expression. The method includes a) providing a sample capable of expressing Myt1; b) incubating the sample with a reagent under conditions where Myt1 is expressed in the absence of the reagent; c) isolating total or polyadenylated RNA from the sample; d) incubating the RNA with a polynucleotide probe specific for a Myt1 nucleic acid of the invention; and e) comparing the effect of the reagent on Myt1 RNA expression relative to a control, wherein any variation compared to control is indicative of a reagent which modulates Myt1 expression.

In another embodiment, the invention provides a method for treating an Myt1-mediated disorder in a patient including administering to the patient a therapeutically effective amount of a reagent that modulates Myt1 activity. Also included is a method of treating an Myt1-associated disorder in a patient, including administering to the patient a therapeutically effective amount of an Myt1 polypeptide or Myt1 nucleic acid.

In a further embodiment, the invention includes a kit useful for the detection of Myt1 polypeptide or polynucleotide, the kit including a carrier means being compartmentalized to receive in close confinement therein one or more containers comprising a first container containing an antibody which binds to Myt1 polypeptide or nucleic acid probes that bind Myt1 polynucleotide, respectively, and a second container containing a detectable label. Preferably, the antibody is a monoclonal antibody.

BRIEF DESCRIPTION OF THE DRAWINGS

FIG. 1A is the predicted amino acid sequence of Myt1. The nucleotide sequence of the Myt1 cDNA (GenBank accession number U28931) contains a predicted open reading frame of 548 amino acids which is preceded by two in-frame termination codons. The catalytic domain (underlined) and a putative transmembrane segment (boxed) are indicated.

FIG. 1B is an alignment of the catalytic domains from Myt1 (row 1), S. pombe Wee1 (row 2, residues 560 to 781), and Xenopus Wee1 (row 3, residues 210 to 443) was performed as described (4). Amino acids that are conserved in all known members of the Wee1 family, but not in other protein kinases, are designated with asterisks. Arrows indicate regions that were used to design degenerate PCR primers.

FIGS. 1D and 1E are the nucleotide sequence of Xenopus Myt1.

FIG. 2A shows phosphorylation analysis of recombinant Myt1 protein from Sf9 cells (even lanes) or a control mock preparation from uninfected cells (odd lanes) incubated with purified Cdc2-cyclin B1 complexes containing the wild-type (WT) or indicated mutant forms of Xenopus Cdc2 in the presence of [$\gamma$-$^{32}$P]ATP. After 15 min at 22° C., samples were processed for autoradiography. Cdc2-P, phosphorylated Cdc2; AF double mutant T14A,Y15F; N133A-AF, triple mutant T14A,Y15F,N133A.

FIG. 2B is a phosphoamino acid analysis of the indicated samples from (A) shows that Myt1 phosphorylates Cdc2 on Thr$^{14}$ and Tyr$^{15}$. For the wild-type and N133A forms or Cdc2, the portion of the autoradiogram containing the dipeptide phosphorylated on both Thr$^{14}$ and Tyr$^{15}$ has not been depicted. S, phosphoserine; T, phosphothreonine; Y, phosphotyrosine.

FIG. 2C is an immunoblot using antibodies to Xenopus Cdc2 of the venous Cdc2-cyclin B complexes shows that similar amounts of substrate were used in FIG. 2A. The reduced electrophoretic mobility of the T161A mutant is due to the lack of phosphorylation on Thr$^{161}$. Both the N133A and N133A-AF mutants appear larger because of the presence of a hemagglutinin tag.

DETAILED DESCRIPTION OF THE INVENTION

Cdc2 is the cyclin-dependent kinase that controls entry of cells into mitosis. Phosphorylation of Cdc2 on threonine-14 and tyrosine-15 inhibits the activity of the enzyme and prevents premature initiation of mitosis. Although Wee1 has been identified as the kinase that phosphorylates tyrosine-15 in various organisms, the threonine-14-specific kinase had not been isolated. A complementary DNA was cloned from Xenopus that encodes Myt1, a member of the Wee1 family, that was discovered to phosphorylate Cdc2 efficiently on both threonine-14 and tyrosine-15. Myt1 is a membrane-associated protein that contains a putative transmembrane segment. Immunodepletion studies suggested that Myt1 is the predominant threonine-14-specific kinase in Xenopus egg extracts. Myt1 activity is highly regulated during the cell cycle, suggesting that this relative of Wee1 plays a role in mitotic control.

Degenerate polymerases chain reaction (PCR) primers (based on the sequence similarity between *S. pombe* Wee1, *S. pombe* Mik1, and human Wee1) were used to amplify a segment of its complementary DNA (cDNA). With a different combination of primers, the inventors amplified a segment of another Xenopus oocyte cDNA that encodes a distinct member of the Wee1 family. After cloning the corresponding full-length cDNA and characterizing its gene product (FIG. 1A), the protein was designated Myt1 for the membrane-associated, tyrosine- and threonine-specific, Cdc2 inhibitory kinase.

Figure 1B:
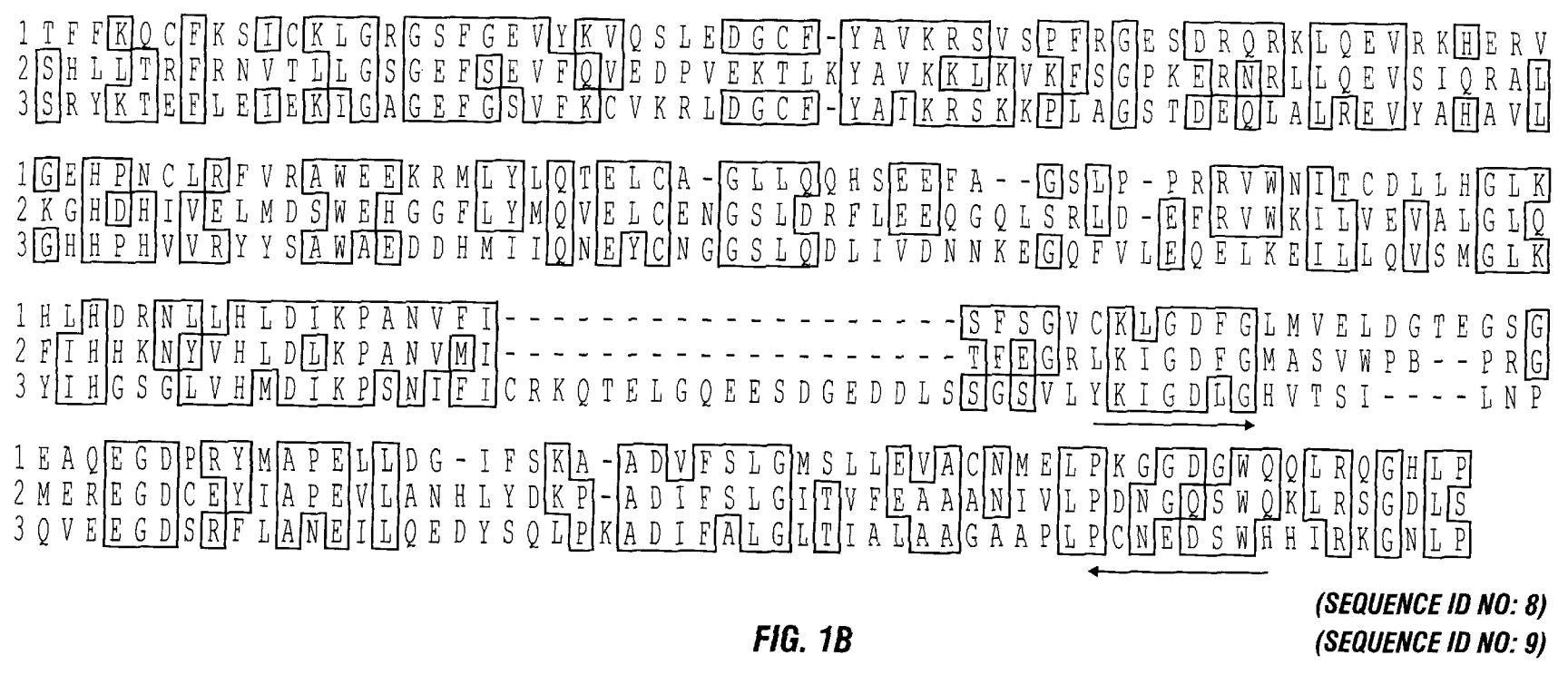

Conceptual translation of the gene encoding Myt1 revealed that it is most similar to kinases in the Wee1 family (FIG. 1B). The kinase domain of Myt1 has a similar degree of sequence similarity with all members of this family, ranging from 40%, identical residues for *S. pombe* Wee1 to 35%, for *S. pombe* Mik1 (R. N. Booher et al., *Embo J.* 12, 3417 (1993); M. Igarashi et al., *Nature,* 353 80 (1991); K. Lundgren et al., *Cell,* 64, 1111 (1991); GenBank accession number Z36752 (*Caenorhabditis elegans*); GenBank accession number U25693 (*Emericella nidulans*)GenBank accession number D30743 (*Mus musculus*). The kinase domain of Myt1 has 39%, identical residues to the previously identified Xenopus Wee1 homolog, whereas Xenopus and human Wee1 share 72% identical residues in this region (P. R. Mueller et al., *Mol. Biol. Cell* 6, 119(1995). This suggests that Myt1 represents a distinct member of the Wee1 family rather than a closely related isoform.

Figure 1C:
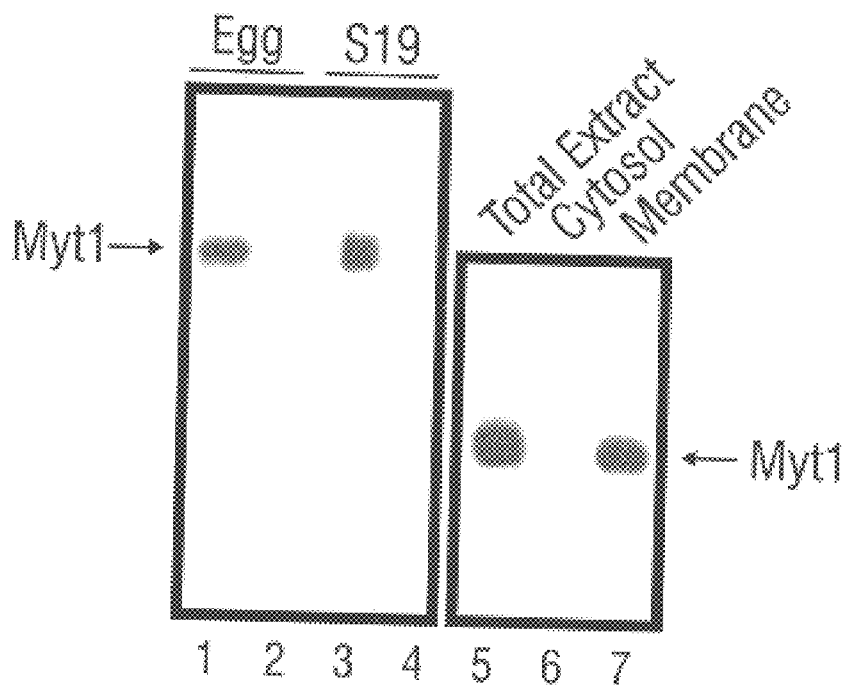
FIG. 1C (Left panel) shows an immunoprecipitation of a Xenopus interphase egg extract was immunoprecipitated with antibodies to Myt1 (anti-Myt1) (lane 1) or control (lane 2) antibodies. Recombinant Myt1 was purified from infected Sf9 cells (lane 3), or a control mock preparation was prepared from uninfected cells (lane 4). All of these preparations were immunoblotted with anti-Myt1. (Right panel) Total interphase egg extract (lane 5) or the cytosol (lane 6) and membrane (lane 7) fractions of the extract (4) were subjected to immunoprecipitation with anti-Myt1 and then immunoblotted with anti-Myt1.

Another distinguishing characteristic of Myt1 is that, unlike other known Wee1 kinases, it contains a potential transmembrane segment, raising the possibility that Myt1 might be an integral membrane protein. This segment is located outside the kinase domain and consists of a stretch of 20 hydrophobic or uncharged amino acids flanked on both ends by a basic residue (lysine or arginine). To examine the subcellular localization of the Myt1 protein, we fractionated Xenopus egg extracts into cytosol and membrane fractions by ultracentrifugation. Subsequently, we washed the membrane fraction with a buffer containing a high concentration of salt to remove weakly associated proteins. After immunoprecipitation and immunoblotting with antibodies to Myt1 (anti-Myt1), nearly all of the Myt1 protein was recovered in the washed membrane fraction, whereas essentially none was found in the cytosol (FIG. 1C). This distribution was observed with both interphase and mitotic extracts (8). In contract, more than 90% of Xenopus Wee1 resides in the egg cytosol fraction (4). Thus, unlike Wee1 , Myt1 appears to be a membrane-associated protein. Because the catalytic domain of Myt1 would presumably reside in the cytosol, Myt1 may be a type II membrane protein with its transmembrane segment serving as an uncleaved, internal signal sequence.

The present invention includes the specific Myt1 disclosed, as well as closely related Myt1s which are identified and isolated by the use of probes or antibodies prepared from the polynucleotide and amino acid sequences disclosed, respectively, for the Myt1 of the invention. This can be done using standard techniques, e.g., by screening a genomic, cDNA, or combinatorial chemical library with a probe having all or a part of the nucleic acid sequences of the disclosed Myt1s. The invention further includes synthetic polynucleotides having all or part of the amino acid sequence of the Myt1 herein described.

In a first embodiment, the invention provides a substantially purified Myt1 polypeptide exemplified by the amino acid sequence of SEQ ID NO:2. The term "polypeptide" means any chain of amino acids, regardless of length or post-translational modification (e.g., glycosylation or phosphorylation), and includes natural proteins as well as synthetic or recombinant polypeptides and peptides.

The term "substantially pure" as used herein refers to Myt1 which is substantially free of other proteins, lipids, carbohydrates or other materials with which it is naturally associated. One skilled in the art can purify Myt1 using standard techniques for protein purification. The substantially pure polypeptide will yield a single major band on a non-reducing polyacrylamide gel. The purity of the Myt1 polypeptide can also be determined by amino-terminal amino acid sequence analysis. Myt1 polypeptide includes functional fragments of the polypeptide, as long as the activity of Myt1 remains (e.g., phosphorylates Cdc2). Smaller peptides containing the biological activity of Myt1 are included in the invention. The term "substantially pure," when referring to an Mty1 polypeptide, means a polypeptide that is at least 60%, by weight, free from the proteins and naturally-occurring organic molecules with which it is naturally associated. A substantially pure Myt1 polypeptide is at least 75%, more preferably at least 90%, and most preferably at least 99%, by weight, Myt1 polypeptide. A substantially pure Myt1 can be obtained, for example, by extraction from a natural source; by expression of a recombinant nucleic acid encoding a Myt1 polypeptide, or by chemically synthesizing the protein. Purity can be measured by any appropriate method, e.g., column chromatography, polyacrylamide gel electrophoresis, or HPLC analysis.

Minor modifications of the recombinant Myt1 primary amino acid sequence may result in proteins which have substantially equivalent activity as compared to the Myt1 polypeptide described herein. Such modifications may be deliberate, as by site-directed mutagenesis, or may be spontaneous. All of the polypeptides produced by these modifications are included herein as long as the biological activity of Myt1 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for Myt1 biological activity.

The polynucleotide sequence encoding the Myt1 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention provides isolated polynucleotides encoding the Myt1 polypeptide. In one embodiment, the polynucleotide is the nucleotide sequence of SEQ ID NO:1. These polynucleotides include DNA, cDNA and RNA sequences which encode Myt1. It is understood that all polynucleotides encoding all or a portion of Myt1 are also included herein, as long as they encode a polypeptide with Myt1 activity (e.g., phosphorylates Cdc2). Such polynucleotides include naturally occurring, synthetic, and intentionally manipulated polynucleotides. For example, Myt1 polynucleotide may be subjected to site-directed mutagenesis. The polynucleotide sequence for Myt1 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of Myt1 polypeptide encoded by the nucleotide sequence is functionally unchanged. Abbreviations for the amino acid residues are follows: A, Ala; C, Cys; D, Asp: E, Glu: F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

As used herein, "polynucleotide" also refers to a nucleic acid sequence of deoxyribonucleotides or ribonucleotides in the form of a separate fragment or a component of a larger construct. DNA encoding portions or all of the polypeptides of the invention can be assembled from cDNA fragments or from oligonucleotides that provide a synthetic gene which can be expressed in a recombinant transcriptional unit.

An isolated polynucleotide as described herein is a nucleic acid molecule that is separated in some way from sequences in the naturally occurring genome of an organism. Thus, the term "isolated polynucleotide" includes any nucleic acid molecules that are not naturally occurring. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences.

Specifically disclosed herein is a DNA sequence containing the Xenopus Myt1 gene. The polynucleotide encoding Myt1 includes FIG. 1A (SEQ ID NO:1), as well as nucleic acid sequences complementary to SEQ ID NO:1. A complementary sequence may include an antisense nucleotide. When the sequence is RNA, the deoxynucleotides A, G, C, and T of SEQ ID NO:1 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO: 2 under physiological conditions or a close family member of Myt1. The term "selectively hybridize" refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the Myt1 polynucleotide of the invention is derived from Xenopus or from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981; Maniatis, et al., *Molecular Cloning: A Laboratory Manual*, Cold Spring Harbor, N.Y. 1989). Thus, one of skill in the art can readily use the Xenopus Myt1 nucleotide sequence of the invention to design a combination of primers for isolating Myt1 from other species (e.g., mouse, rat or human).

The development of specific DNA sequences encoding Myt1 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for Myt1 peptides having at least one epitope, using antibodies specific for Myt1. Such antibodies can be either polyclonally or monoclonally derived and used to detect expression product indicative of the presence of Myt1 cDNA.

The isolated polynucleotide sequences of the invention also include sequences complementary to the polynucleotides encoding Myt1 (antisense sequences). Antisense nucleic acids are DNA or RNA molecules that are complementary to at least a portion of a specific mRNA molecule (Weintraub et al., Scientific American 262:40, 1990). The invention includes all antisense polynucleotides that inhibit production of Myt1 polypeptides. In the cell, the antisense nucleic acids hybridize to the corresponding mRNA, forming a double-stranded molecule. Antisense oligomers of about 15 nucleotides are preferred, since they are easily synthesized and introduced into a target Myt1-producing cell. The use of antisense methods to inhibit the translation of genes is known in the art, and is described, e.g., in Marcus-Sakura (Anal. Biochem., 172:289, 1988).

In addition, ribozyme nucleotide sequences for Myt1 are included in the invention. Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech (1988) J. Amer. Med. Assn. 260:3030). A major advantage of this approach is that, because they are sequence-specific, only mRNAs with particular sequences are inactivated.

There are two basic types of ribozymes, tetrahymena-type (Hasselhoff (1988) Nature 334:585) and "hammerhead"-type. Tetrahymena-type ribozymes recognize sequences which are four bases in length, while "hammerhead"-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating a specific mRNA species, and 18-base recognition sequences are preferable to shorter recognition sequences.

DNA sequences encoding Myt1 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the Myt1 polynucleotide sequences may be inserted into a recombinant expression vector. The term "recombinant expression vector" refers to a plasmid, virus or other vehicle known in the art that has been manipulated by insertion or incorporation of the Myt1 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding Myt1 can be expressed in either prokaryote or eukaryotes. Hosts can include microbial, yeast, insect and mammalian organisms. Methods of expressing DNA sequences having eukaryotic or viral sequences in prokaryote are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the Myt1 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The present invention also provides antibodies useful for detecting Mty1 polypeptide. The preparation of polyclonal antibodies is well-known to those skilled in the art. See, for example, Green et al., *Production of Polyclonal Antisera*, in IMMUNOCHEMICAL PROTOCOLS (Manson, ed.), pages 1–5 (Humana Press 1992); Coligan et al., *Production of Polyclonal Antisera in Rabbits, Rats, Mice and Hamsters*, in CURRENT PROTOCOLS IN IMMUNOLOGY, section 2.4.1 (1992), which are hereby incorporated by reference.

The preparation of monoclonal antibodies likewise is conventional. See, for example, Kohler & Milstein, *Nature* 256:495 (1975); Coligan et al., sections 2.5.1–2.6.7; and Harlow et al., ANTIBODIES: A LABORATORY MANUAL, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., *Purification of Immunoglobulin G* (IgG), in METHODS IN MOLECULAR BIOLOGY, VOL. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., *Int. J. Cancer* 46:310 (1990), which are hereby incorporated by reference.

Alternatively, a therapeutically useful anti-Myt1 antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989), which is hereby incorporated in its entirety by reference. Techniques for producing humanized monoclonal antibodies are described, for example, by Jones et al., *Nature* 321:522 (1986); Riechmann et al., *Nature* 332:323 (1988); Verhoeyen et al., *Science* 239:1534 (1988); Carter et al., *Proc. Nat'l Acad. Sci. USA* 89:4285 (1992); Sandhu, *Crit. Rev. Biotech.* 12:437 (1992); and Singer et al., *J. Immunol.* 150:2844 (1993), which are hereby incorporated by reference.

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., *Ann. Rev. Immunol.* 12:433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6:579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and U.S. Pat. No. 4,331,647, and references contained therein. These patents are hereby incorporated in their entireties by reference. See also Nisonhoff et al., *Arch. Biochem. Biophys.* 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., *Science* 242:423–426 (1988); Ladner et al., U.S. Pat. No. 4,946,778; Pack et al., *Bio/Technology* 11:1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

The invention also provides methods of identifying subjects at risk for Myt1-mediated disorders by measuring activation of the Myt1 mitotic regulation pathway. Activation of Myt1 can be determined by measuring Myt1 synthesis; activation of Myt1 isoforms; or activation of Myt1 substrate Cdc2. The term "Myt1 substrate" as used herein includes Myt1 substrates (e.g., Cdc2), as well as Myt1 substrate substrates (e.g., Cdc25).

In one embodiment, activation of the Myt1 pathway is determined by measuring activation of the appropriate Myt1 pathway substrates (e.g., Cdc2). Myt1 activity is measured by the rate of substrate phosphorylation as determined by quantitation of the rate of labeled phosphorus (e.g., $[^{32}]P$ or $[^{33}]P$) incorporation at $Thr^{14}$ of Cdc2, for example. This can also be measured using phosphorylation-specific reagents, such as antibodies. The specificity of Myt1 substrate phosphorylation can be tested by measuring cell proliferation for example, or by employing mutated Cdc2 molecules that lack the sites for Myt1 phosphorylations (e.g., $Thr^{14}$ or $Tyr^{15}$, or both). FIG. 2 and the Examples provide examples of mutated Cdc2 molecules for such assays. Altered phosphorylation of the substrate relative to control values indicates alteration of the Myt1 mitotic regulation pathway, and detects increased risk in a subject of an Myt1-mediated disorder. Myt1 activation can be detected with the substrate Cdc2. Cdc2 is incubated with a test sample in which Myt1 activity is to be measured and [γ-32P]ATP, under conditions sufficient to allow the phosphorylation of Cdc2. Cdc2 is then isolated and the amount of phosphorylation quantitated. In a specific embodiment, Cdc2 is isolated by immunoprecipitation, resolved by SDS-PAGE, and detected by autoradiography (see Examples).

In another embodiment, activation of the Myt1 pathway is determined by measuring the level of Myt1 expression in a test sample. In a specific embodiment, the level of Myt1 expression is measured by Western blot analysis. The proteins present in a sample are fractionated by gel electrophoresis, transferred to a membrane, and probed with labeled antibodies to Myt1. In another specific embodiment, the level of Myt1 expression is measured by Northern blot analysis. Total cellular or polyadenylated [poly(A)+] mRNA is isolated from a test sample. The RNA is fractionated by electrophoresis and transferred to a membrane. The membrane is probed with labeled Myt1 cDNA. Myt1 expression can also be measured by quantitative PCR applied to expressed mRNA.

Myt1 activity, synthesis, expression and the like can be tested for example in a cell or in a test sample from virtually any source. Test samples include biological test samples such as fluid, cells, or tissue obtained for example from a mammal. The biological test sample includes a sample containing yeast cells.

In another embodiment, the invention provides a method for identifying an agent, reagent, or compound that modulates Myt1 activity. The term "modulation of Myt1 activity" includes inhibitory or stimulatory effects. The method includes a) obtaining a test sample containing Myt1; b) incubating the test sample with a substrate for the Myt1, the reagent, and labeled phosphate under conditions sufficient to allow phosphorylation of the substrate in the absence of the reagent; c) detecting phosphorylation of the substrate; and d) comparing the effect of the reagent on Myt1 activity relative to a control not containing the reagent, wherein any variation compared to control is indicative of a reagent which modulates Myt1 substrate phosphorylation. Accordingly, in one aspect, the invention features methods for identifying a reagent which modulates Myt1 activity, by incubating Myt1 with the test reagent and measuring the effect of the test reagent on Myt1 synthesis, expression, phosphorylation, function, or activity. In one aspect, the effect of the test reagent on Myt1 synthesis is measured by Western blot analysis using an antibody to Myt1. In another aspect, the effect of a reagent on Myt1 activity is measured by incubating Myt1 with the test reagent, $^{32}$P-ATP, and a substrate in the Myt1 pathway (e.g., Cdc2 or a fragment thereof containing at least $Thr^{14}$). The rate of substrate phosphorylation is determined as described above and in the Examples. In another aspect, the test reagent is incubated with a cell transfected with an Myt1 polynucleotide expression vector, and the effect of the test reagent on Myt1 transcription is measured by Northern blot analysis, as described above.

The invention is useful for screening reagents that modulate Myt1 activity or expression as described above. Myt1 disorders may result in either premature progression of the cell through mitosis or inhibition of normal progression of the cell through mitosis, for example. In one aspect, the invention provides reagents which inhibit Myt1 activity or expression, for example, in situations where the Myt1 disorder cause cells to arrest in the G2 phase of the cell cycle. Such reagents are useful for the treatment or prevention of Myt1-mediated disorders, for example, disorders in which it is desirable to stimulate cell progression into mitosis. Such reagents include Myt1 antibodies and antisense for example.

Alternatively, the invention is useful for screening reagents that enhance Myt1 activity. Such reagents are useful for the treatment or prevention of Myt1-mediated disorders, for example, disorders in which there is premature entry into mitosis. Such reagents include sense Myt1 polynucleotides or Myt1 polypeptides.

Therefore, the invention further features a method of treating a Myt1-mediated disorder by administering to a subject in need thereof, an effective dose of a therapeutic reagent that inhibits or stimulates the activity of Myt1.

Anti-myt1 reagents identified in the present invention can have important medical consequences and may be further tested for use in treating proliferative diseases which include a wide range of cancers, neoplasias, and hyperplasias, as well as for general or specific immunosuppression, such as through inhibition of the proliferation of lymphocytes. In addition, the assays of the invention can be used to identify anti-mitotic agents which can be used in the treatment of pathogenic infections such as fungal infections which give rise to mycosis. Anti-mitotic agents identified in the present assay may also be used, for example, in birth control methods by disrupting orogenic pathways in order to prevent the development of either the egg or sperm, or by preventing mitotic progression of a fertilized egg.

Agents identified that enhance Myt1 activity are useful for example to develop inhibitors of fungal infections. The most common fungal infections are superficial and are presently treated with one of several topical drugs or with the oral drugs ketoconazole or griseofulvin. The systemic mycoses constitute quite a different therapeutic problem. These infections are often very difficult to treat and long-term, parenteral therapy with potentially toxic drugs may be required. The systemic mycoses are sometimes considered in two groups according to the infecting organism. The "opportunistic infections" refer to those mycoses-candidiasis, aspergillosis, cryptococcosis, and phycomycosis-that commonly occur in debilitated and immunosuppressed patients. These infections are a particular problem in patients with leukemias and lymphomas, in people who are receiving immunosuppressive therapy, and in patients with such predisposing factors as diabetes mellitus or AIDS. Other systemic mycoses-for example, blastomycosis, histoplasmosis, coccidioidomycosis, and sporotrichosis-tend to have a relatively low incidence that may vary considerably according to geographical area.

By way of illustration, the present invention can be used to screen for anti-mitotic agents able to inhibit at least one fungus implicated in such mycosis as candidiasis, aspergillosis, mucormycosis, blastomycosis, geotrichosis, cryptococcosis, chromoblastomycosis, coccidioidomycosis, conidiosporosis, histoplasmosis, maduromycosis, rhinosporidiosis, nocardiosis, para-actinomycosis, penicilliosis, moniliasis, or sporotrichosis. For example, if the mycotic infection to which treatment is desired is candidiasis, the present assay can comprise either a hyper-mitotic (e.g., underexpression of Myt1) or hypo-mitotic (e.g., overexpression of Myt1) cells generated directly from, or with genes cloned from, yeast selected from the group consisting of Candida albicans, Candida stellatoidea, Candida tropicalis, Candida parapsilosis, Candida krusei, Candida pseudotropicalis, Candida quillermondii, and Candida rugosa. Likewise, the present assay can be used to identify anti-mitotic and anti-meiotic agents which may have therapeutic value in the treatment of aspergillosis by making use of yeast such as Aspergillus fumigatus, Aspergillus flavus, Aspergillus niger, Aspergillus nidulans, or Aspergillus terreus. Where the mycotic infection is mucormycosis, the yeast can be selected from a group consisting of Rhizopus arrhizus, Rhizopus oryzae, Absidia corymbifera, Absidia ramosa, and Mucor pusillus. Another pathogen which can be utilized in the present assay is Pneumocystis carinii.

Agents to be tested for their ability to act as anti-mitotic agents in the present invention can be those produced by bacteria, yeast or other organisms, or those produced chemically. The assay can be carried out in any vessel suitable for the growth of the cell, such as microtiter plates or petri dishes. As potent inhibitors mitosis can fully inhibit proliferation of a cell, it may be useful to perform the assay at various concentrations of the candidate agent. For example, serial dilutions of the candidate agents can be added to the hyper-mitotic cell such that at least one concentration tested the anti-mitotic agent inhibits the mitotic activator to an extent necessary to adequately' slow the progression of the cell through the cell-cycle but not to the extent necessary to inhibit entry into mitosis all together. In a like manner, where the assay comprises a hypo-mitotic cell, serial dilutions of a candidate agent can be added to the cells such that, at least one concentration, an anti-mitotic agent inhibits Myt1 to an extent necessary to adequately enhance progression of the cell through the cell-cycle, but not to an extent which would cause mitotic catastrophe.

Quantification of proliferation of the hyper-mitotic cell in the presence and absence of a candidate agent can be measured with a number of techniques well known in the art, including simple measurement of population growth curves. For instance, where the assay involves proliferation in a liquid medium, turbidimetric techniques (i.e. absorbance/transmittance of light of a given wavelength through the sample) can be utilized. For example, in the instance where the reagent cell is a yeast cell, measurement of absorbance of light at a wavelength between 540 and 600 nm can provide a conveniently fast measure of cell growth.

Likewise, ability to form colonies in solid medium (e.g. agar) can be used to readily score for proliferation. Both of these techniques, especially with respect to yeast cells, are suitable for high through-put analysis necessary for rapid screening of large numbers of candidate agents. In addition, the use of solid media such as agar can further aid in establishing a serial dilution of the candidate agent. For example, the candidate agent can be spotted on a lawn of reagent cells plated on a solid media. The diffusion of the candidate agent through the solid medium surrounding the site at which it was spotted will create a diffusional effect. For anti-mitotic agents scored for a halo of cell growth would be expected in an area which corresponds to concentrations of the agent which offset the effect of the impaired checkpoint, but which are not so great as to over-compensate for the impairment or too little so as to be unable to rescue the cell.

To further illustrate, other proliferative scoring techniques useful in the present assay include measuring the mitotic index for untreated and treated cells; uptake of detectable nucleotides, amino acids or dyes; as well as visual inspection of morphological details of the cell, such as chromatin structure or other features which would be distinguishable between cells advancing appropriately through mitosis and cells concluding in mitotic catastrophe or stuck at certain cell-cycle checkpoint. In the instance of scoring for meiosis, morphology of the spores or gametes can be assessed. Alternatively, the ability to form a viable spore of gamete can be scored as, for example, measuring the ability of a spore to re-enter negative growth when contacted with an appropriate fermentable media.

An "Myt1-mediated disorder" is a pathological condition resulting, at least in part, from excessive or insufficient activation of Myt1. Myt1-mediated disorders include, for example, ischemic heart disease, burns due to heat or radiation (UV, X-ray, $\gamma$, $\beta$, etc.), kidney failure, liver damage due to oxidative stress or alcohol, respiratory distress syndrome, septic shock, rheumatoid arthritis, autoimmune disorders, and other types of inflammatory diseases.

A "therapeutic reagent" any compound or molecule that achieves the desired effect on an Myt1-mediated disorder when administered to a subject in need thereof.

Myt1-mediated disorders further include proliferative disorders. Examples of Myt1-mediated proliferative disorders are psoriasis, acquired immune deficiency syndrome, malignancies of various tissues of the body, including malignancies of the skin, bone marrow, lung, liver, breast, gastrointestinal system, and genito-urinary tract. Preferably, therapeutic reagents which enhance the activity or expression of Myt1 inhibit cell growth.

A therapeutic reagent that "enhances Myt1 activity" interferes with a Myt1-regulated mitosis pathway. For example, a therapeutic reagent can alter the protein kinase activity of Myt1, increase the level of Myt1 transcription or translation, or increase Myt1 phosphorylation of Cdc2, thus disrupting the Myt1-regulated mitotic pathway. Examples of such reagents include antibodies that bind specifically to Cdc25 polypeptides, and fragments of Myt1 polypeptides that competitively inhibit Cdc25 polypeptide activity.

A therapeutic reagent that "enhances Myt1 activity" supplements a Myt1 regulated mitotic pathway. Examples of such reagents include the Myt1 polypeptides themselves, which can be administered in instances where the Myt1-mediated disorder is caused by underexpression of the Myt1 polypeptide, or expression of a mutant Myt1 polypeptide. In addition, portions of DNA encoding an Myt1 polypeptide can be introduced into cells that underexpress an Myt1 polypeptide.

A "therapeutically effective amount" is an amount of a reagent sufficient to decrease or prevent the symptoms associated with the Myt1-mediated disorder.

Therapeutic reagents for treatment of Myt1-mediated disorders identified by the methods of the invention are administered to a subject in a number of ways known to the art, including parenterally by injection, infusion, sustained-release injection or implant, intravenously, intraperitoneally, intramuscularly, subcutaneously, or transdermally. Epidermal disorders and disorders of the epithelial tissues are treated by topical application of the reagent. The reagent is mixed with other compounds to improve stability and efficiency of delivery (e.g., liposomes, preservatives, or dimethyl sulfoxide (DMSO)). Polynucleotide sequences, including antisense sequences, can be therapeutically administered by techniques known to the art resulting in introduction into the cells of a subject suffering from the Myt1-mediated disorder. These methods include the use of viral vectors (e.g., retrovirus, adenovirus, vaccinia virus, or herpes virus), colloid dispersions, and liposomes.

The materials of the invention are ideally suited for the preparation of a kit for the detection of the level or activity of Myt1. Accordingly, the invention features a kit comprising an antibody that binds Myt1, or a nucleic acid probe that hybridizes to a Myt1 polynucleotide, and suitable buffers. The probe or monoclonal antibody can be labeled to detect binding to a Myt1 polynucleotide or protein. The label is selected from the group consisting of a radioisotope, a bioluminescent compound, a chemiluminescent compound, a fluorescent compound, a metal chelate, or an enzyme for example.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, and from the claims. The following examples are intended to illustrate but not limit the invention. While they are typical of those that might be used, other procedures known to those skilled in the art may alternatively be used.

EXAMPLES

The present examples show the identification of Myt1, a distinct member of the Wee1 family that collaborates with Wee1 by phosphorylating Cdc2 on Thr$^{14}$ in addition to Tyr$^{15}$. Collectively, the inhibitory Wee1 and Myt1 kinases ensure that Cdc2 at vary locations throughout the cell becomes a activated only at the G$_2$-M transition.

Example 1

Isolation and Characterization of Myt1

Previously, the inventors isolated a Xenopus Wee1 homolog. Degenerate polymerases chain reaction (PCR) primers (based on the sequence similarity between *S. pombe* Wee1, *S. pombe* Mik1, and human Wee1) were used to amplify a segment of its complementary DNA (cDNA) (P. R. Mueller et al., *Mol. Biol. Cell* 6, 119(1995). With a different combination of primers, a segment of another Xenopus oocyte cDNA that appears to encode a distinct member of the Wee1 family was amplified. After cloning the corresponding full-length cDNA and characterizing its gene product, we designated this protein Myt1 for the membrane-associated, tyrosine- and threonine-specific, Cdc2 inhibitory kinase. FIG. 1A is the predicted amino acid sequence of Myt1 and FIG. 1D is the nucleotide sequence of Xenopus Myt1. An internal fragment of the Myt1 cDNA was amplified by PCR as described (P. R. Mueller et al., supra) except that the annealing temperature was 45° C. for the first five cycles and 55° C. for the remaining 30 cycles. The 5' and 3' primers were CGGGGTACC(C/T)T(A/G)AA(I/C)(C/T/A)TIGGIGA(T/C)(T/C)T(I/C)GG (SEQ ID NO:3) and TCCCCCGGGTGCCAI(T/G/C)II(T/A) (C/G)ICC(G/A)TT(I/C) (C/T)(G/T/'C)(I/C)GG (SEQ ID NO:4), respectively. This reaction yielded a 221-base pair fragment that was used to isolate a full-length Myt1 cDNA from a Xenopus oocyte library as described (P. R. Mueller et al., supra).

The nucleotide sequence of the Myt1 cDNA (GenBank accession number U28931) contains a predicted open reading frame of 548 amino acids which is preceded by two in-frame termination codons. The catalytic domain (underlined) and a putative transmembrane segment (boxed) are indicated.

Conceptual translation of the gene encoding Myt1 revealed that it is most similar to kinases in the Wee1 family. FIG. 1B is an alignment of the catalytic domains from Myt1 (row 1), S. pombe Wee1 (row 2, residues 560 to 781), and Xenopus Wee1 (row 3, residues 210 to 443) was performed as described (P. R. Mueller et al., Mol. Biol. Cell 6, 119 (1995). Amino acids that are conserved in all known members of the Wee1 family, but not in other protein kinases, are designated with asterisks. Arrows indicate regions that were used to design degenerate PCR primers.

The kinase domain of Myt1 has a similar degree of sequence similarity with all members of this family, ranging from 40%, identical residues for S. pombe Wee1 to 35%, for S. pombe Mik1 (R. N. Booher et al., EMBO J. 12, 3417 (1993); M. Igarashi et al., Nature 353, 80 (1991); K. Lundgren et al., Cell 64, 1111 (1991); GenBank accession number Z36752 (Caenorhabditis elegans); GenBank accession number U25693 (Emericella nidulans); GenBank accession number D30743 (Mus musculus). The kinase domain of Myt1 has 39%, identical residues to the previously identified Xenopus Wee1 homolog, whereas Xenopus and human Wee1 share 72% identical residues in this region. This suggests that Myt1 represents a distinct member of the Wee1 family rather than a closely related isoform.

Another distinguishing characteristic of Myt1 is that, unlike other known Wee1 kinases, it contains a potential transmembrane segment, raising the possibility that Myt1 might be an integral membrane protein. This segment is located outside the kinase domain and consists of a stretch of 20 hydrophobic or uncharged amino acids flanked on both ends by a basic residue (lysine or arginine). To examine the subcellular localization of the Myt1 protein, we fractionated Xenopus egg extracts into cytosol and membrane fractions by ultracentrifugation.

Subsequently, the membrane fraction was washed with a buffer containing a high concentration of salt to remove weakly associated proteins. After immunoprecipitation and immunoblotting with antibodies to Myt1 (anti-Myt1), nearly all of the Myt1 protein was recovered in the washed membrane fraction, whereas essentially none was found in the cytosol. FIG. 1C (Left panel) shows an immunoprecipitation of a Xenopus interphase egg extract was immuno precipitated with antibodies to Myt1 (anti-Myt1) (lane 1) or control (lane 2) antibodies (Rabbit antibodies to the COOH terminal-end of Myt1 (CNLLGMFDDATEQ) (SEQ ID NO:5) were affinity-purified. Affinity-purified rabbit antibodies to mouse immunoglobulin G (Cappel) served in control experiments. All other antibodies were described previously (A. Kumagai et al., Mol.. Biol. Cell 6, 199 (1995), Endogenous Myt1 was immunoprecipitated from Xenopus egg extracts with anti-Myt1 as described (P. R. Mueller et al., supra) except that 0.5% Triton X-100 replaced NP-40).

Recombinant Myt1 was purified from infected Sf9 cells (lane 3), or a control mock preparation was prepared from uninfected cells (lane 4). A baculovirus expression vector (pVL-HIS-XeMyt1) encoding a histidine-tagged version or Myt1 was prepared with PCR to convert the initiation codon to an NdeI site as described (P. R. Mueller et al., Mol. Biol. Cell 6, 119(1995). The 5' primer was CGGCATATGCCT-GTTCCAGGGGATG (SEQ ID NO:6) and the primer was CAAGGCTTTGCACCTTGTATACCTC (SEQ ID NO:7). Recombinant Myt1 protein was produced in adherent Sf9 insect cells and bound to nickel-i-minidoacetic acid beads (A. Kumagai et al., Mol.. Biol. Cell 6, 199 (1995). The Myt1-containing beads were then washed four times in lysis buffer [10 mM Hepes NaOH (pH 7.4), 150 mM NaCl, 5 mM EGTA, 0.5% Triton X-100, 0.2 mM phenylmethylsulfonyl fluoride and protease inhibitor mix (10 μg each of pepstatin, chymostatin, and leupeptin per milliliter)] and then washed four times in wash buffer (lysis buffer without EGTA and Triton X-100). Recombinant Myt1 protein was eluted from the beads with 150 mM imidazole in wash buffer, frozen in liquid nitrogen, and stored at −80° C. A mock preparation was prepared in the same manner from uninfected Sf9 cells).

All of these preparations were immunoblotted with anti-Myt1. (Right panel) Total interphase egg extract (lane 5) or the cytosol (lane 6) and membrane (lane 7) fractions of the extract were subjected to immunoprecipitation with anti-Myt1 and then immuno blotted with anti-Myt1.

This distribution was observed with both interphase and mitotic extracts. In contrast, more than 90% of Xenopus Wee1 resides in the egg cytosol fraction. Thus, unlike Wee1, Myt1 appears to be a membrane-associated protein. Because the catalytic domain of Myt1 would presumably reside in the cytosol, Myt1 may be a type II membrane protein with its transmembrane segment serving as an uncleaved, internal signal sequence.

To examine the enzymatic properties of Myt1, a histidine-tagged version of the protein in a baculoviral expression system (FIG. 1C) was produced. Myt1 was incubated in the presence of [γ-$^{32}$p]adenosine triphosphate (ATP) and a recombinant Cdc2-cyclin B complex that was purified from baculovirus-infected insect cells. The Cdc2-cyclin complex was prepared under conditions that allow the phosphorylation of the Cdc2 subunit on Thr$^{161}$ through the action of an endogenous insect cell CAK. Recombinant Myt1 efficiently phosphorylated cyclin-associated, wild-type Cdc2, whereas a preparation from uninfected cells contained no kinase activity (FIG. 2A). Myt1 did not phosphorylate monomeric Cdc2, indicating that this reaction is cyclin-dependent.

FIG. 2A shows phosphorylation analysis of recombinant Myt1 protein from Sf9 cells (even lanes) or a control mock preparation from uninfected cells (odd lanes) incubated with purified Cdc2-cyclin B1 complexes containing the wild-type (WT) or indicated mutant forms of Xenopus Cdc2 (A. Kumagai et al. supra) in the presence of [γ-$^{32}$P]ATP. After 15 min at 22° C., samples were processed for autoradiography. Cdc2-P, phosphorylated Cdc2; AF double mutant T14A, Y15F; N133A-AF, triple mutant T14A,Y15F,N133A.

FIG. 2B is a phosphoamino acid analysis (W. J. Boyle et al., Methods Enzymol. 201, 110 (1991) of the indicated samples from (A) shows that Myt1 phosphorylates Cdc2 on Thr$^{14}$ and Tyr$^{15}$. For the wild-type and N133A forms or Cdc2, the portion of the autoradiogram containing the dipeptide phosphorylated on both Thr$^{14}$ and Tyr$^{15}$ has not been depicted. S, phosphoserine; T, phosphothreonine; Y, phosphotyrosine.

Phosphoamino acid analysis of Cdc2 phosphorylated by Myt1 revealed that the $^{32}$P was distributed between both phosphotyrosine (20%) and phosphothreonine (77%) (FIG. 2B). Thus, in contrast to human and Xenopus Wee1, Myt1 phosphorylates Cdc2 on threonine as well as on tyrosine. To assess which residues on Cdc2 were phosphorylated by Myt1, various Cdc2 mutants were used with non-phosphorylatable amino acids at key positions (FIG. 2A). Myt1 can phosphorylate both the TI4A (Thr$^{14}$ changed to Ala) and Y15F (Tyr$^{15}$ changed to Phe) mutants of Cdc2. In contrast, the T14A,Y15F double mutant was not a substrate for Myt1. Phosphoamino acid analysis of $^{32}$P-labeled T14A and Y15F mutants revealed that the TI4A mutant contained 89% of its label in phosphotyrosine, and that nearly all of the $^{32}$P present in the Y15F mutant was in phosphothreonine (96%) (FIG. 2B). Phosphoamino acid analysis consistently revealed a low amount of phosphoserine in the wild-type and mutant T14A and Y15F forms of Cdc2. This serine phosphorylation could result from activity of Myt1 or from weak autophosphorylation by Cdc2 because we used a catalytically active form of Cdc2 as the substrate in these assays. The latter possibility is preferred on the basis of experiments with the catalytically inactive N133A (Asn$^{133}$ changed to Ala) mutant of Cdc2. In particular, phosphoamino acid analysis of the N133A mutant phosphorylated by Myt1 (FIG. 2, A and B) revealed the presence of mainly phosphothreonine (75%) and phosphotyrosine (24%), but essentially no phosphoserine (<0.7%). As expected. the triple mutant T14A,Y15F, N133A was not a substrate for Myt1 (FIG. 2A).

FIG. 2C is an immunoblot using antibodies to Xenopus Cdc2 of the venous Cdc2-cyclin B complexes shows that similar amounts of substrate were used in FIG. 2A. The reduced electrophoretic mobility of the T161A mutant is due to the lack of phosphorylation on Thr$^{161}$. Both the- N133A and N133A-AF mutants appear larger because of the presence of a hemagglutinin tag.

Taken together, these results indicate that Myt1 is a dual-specificity kinase that can efficiently phosphorylate Cdc2 both on Thr$^{14}$ and Tyr$^{15}$. There does not appear to be any obligatory order to the phosphorylation of Cdc2 at these two sites, because both the TI4A and Y15F single mutants of Cdc2 are substrates for Myt1. However, wild-type Cdc2 appears to be phosphorylated more efficiently than either single mutant. Unlike Xenopus Wee1, Myt1 appears to require prior phosphorylation of Cdc2 on Thr$^{161}$ in order for Cdc2 to be a substrate. Consistent with this observation, Myt1 did not phosphorylate the T161A mutant of Cdc2 (FIG. 2A) on either tyrosine or threonine. In addition, like Mik1 (M. S. Lee et al., *J. Biol. Chem.,* 269, 30530, 1994), but unlike other Wee1 homologs (P. R. Mueller et al., supra; C. H. McGowan et al., *EMBO J.,* 12, 75 (1993); L. L. Parker et al., *Science,* 257, 1955 (1992); C. Featherstone et al., *Nature,* 349, 808 (1991)), Myt1 does not have detectable autophosphorylation activity.

Example 2

Myt1 Phosphorylation of Cdc2

The kinase activity of Cdc2 was examined to see if it could be altered by Myt1-mediated phosphorylation. Wild-type and mutant forms of Cdc2 were incubated with Myt1 in the presence of an ATP-regenerating system and subsequently measured the Cdc2-associated histone H1 kinase activity (FIG. 3).

Figure 3A:
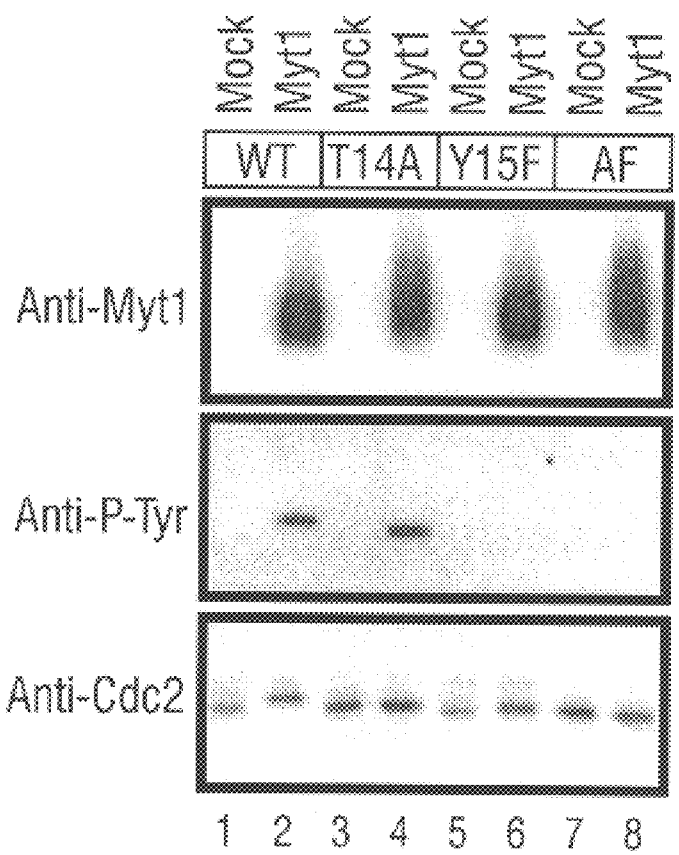
FIG. 3A is an immunoblot of recombinant Myt1 protein from Sf9 cells (even lanes) or a control preparation (mock) from uninfected cells (odd lanes) incubated with purified Cdc2-cyclin B1 complexes containing the wild-type (WT) or indicated mutant forms of Xenopus Cdc2 in the presence of an ATP-regenerating system. After 30 min at 22° C., the samples were processed for immunoblotting with anti-Myt1 (top panel), anti-phosphotyrosine (middle panel), or anti-Cdc2 (bottom panel).

FIG. 3A is an immunoblot of recombinant Myt1 protein from Sf9 cells (even lanes) or a control preparation (mock) from uninfected cells (odd lanes) incubated with purified Cdc2-cyclin B1 complexes containing the wild-type (WT) or indicated mutant forms of Xenopus Cdc2 in the presence of an ATP-regenerating system (The conditions for in vitro kinase assays of Myt1 were as described (P. R. Mueller et al., supra) for Wee1 except that 0.05% Triton X-100 was added. After 30 min at 22° C., the samples were processed for immunoblotting with anti-Myt1 (top panel), anti-phosphotyrosine (middle panel), or anti-Cdc2 (bottom panel).

Figure 3B:
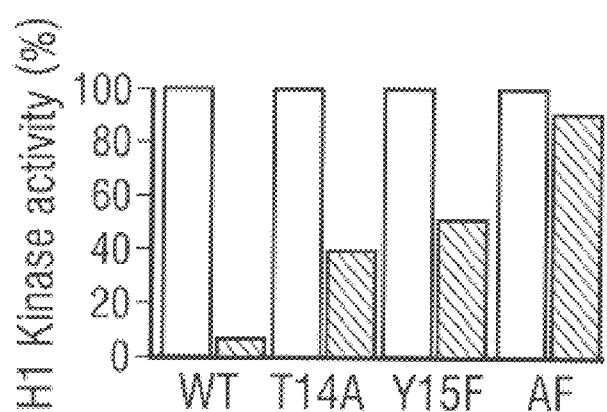
FIG. 3B shows a plot of Cdc2-associated H1 kinase activity of the samples shown in (A) in the presence (stripped bars) or absence (open bars) of Myt1. The graph shows the percentage of H1 kinase activity (normalized for each mutant; 100% equals the activity of the sample in the absence of Myt1).

FIG. 3B shows a plot of Cdc2-associated H1 kinase activity of the samples shown in (A) in the presence (stripped bars) or absence (open bars) of Myt1. The graph shows the percentage of H1 kinase activity (normalized for each mutant; 100% equals the activity of the sample in the absence of Myt1).

In these experiments, phosphorylation of Cdc2 was assessed either by immunoblotting with antibodies to phosphotyrosine or by observing the reduced mobility of modifier Cdc2 during gel electrophoresis. The wild-type Cdc2 protein that had been treated with Myt1 reacted strongly with antibodies to phosphotyrosine and displayed the characteristic double shift (B. A. Edgar et al., *Genes Dev.* 8, 440, 1994; M. Solomon et al., *Mol. Biol. Cell,* 3, 13, 1992) in SDS-polyacrylamide gels indicative of phosphorylation on both Thr$^{14}$ and Tyr$^{15}$ (FIG. 3A). The same analysis showed that the T14A and Y15F mutants are single-shifted as a result of phosphorylation at only one site. Treatment of wild-type Cdc2 with Myt1 caused a 90% reduction in its H1 kinase activity. Similarly, phosphorylation of both the T14A and Y15F mutants by Myt1 resulted in a large reduction in activity (60 and 50%, respectively). As expected, the T14A, Y15F double mutant of Cdc2 was neither phosphorylated nor inactivated by Myt1 (FIG. 3, A and B). Collectively, these experiments indicate that phosphorylation of Thr$^{14}$ and Tyr$^{15}$ or both by Myt1 leads to a substantial reduction in the catalytic activity of Cdc2.

Figure 4A:
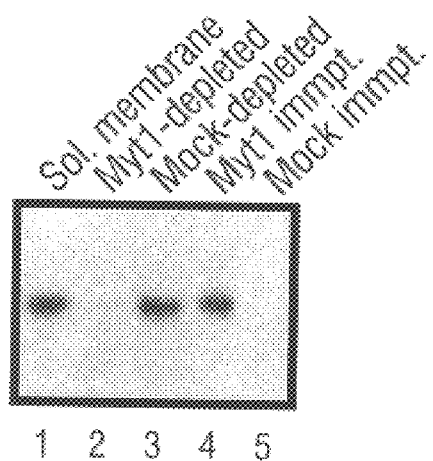
FIG. 4A is an immunoblot of the membrane fraction of an interphase Xenopus egg extract was solubilized with Triton X-100 (lane 1) and either treated with anti-Myt1 (lanes 2 and 4) or with control antibodies (lanes 3 and 5). Protein A beads were added, incubated, and removed along with associated proteins. The solubilized membrane fraction (lane 1), depleted supernatants (lanes 2 and 3), and isolated beads (lanes 4 and 5) were immunoblotted with anti-Myt1. Immpt., immunoprecipitate.

FIG. 4A is an immunoblot of the membrane fraction of an interphase Xenopus egg extract was solubilized with Triton X-100 (lane 1) and either treated with anti-Myt1 (lanes 2 and 4) or with control antibodies (lanes 3 and 5). Protein A beads were added, incubated, and removed along with associated proteins as described An interphase extract from Xenopus eggs was made in the presence of cycloheximide (100 µg/ml) as described (P. R. Mueller et al., *Mol. Bio. Cell.* 6, 119 (1995). All subsequent steps were done on ice or at 4° C. The extract was diluted with two volumes of DB [20 mM Hepes (pH 7.6). 100 mM NaCl. 5 mM NaF, 1 mM $Na_4P_2O_7$ 1 mM dithiothreitol. and protease inhibitor mix. The Myt1-containing beads were then washed four times in lysis buffer [10 mM Hepes NaOH (pH 7.4), 150 mM NaCl, 5 mM EGTA, 0.5% Triton X-100, 0.2 mM phenylmethylsulfonyl fluoride and protease inhibitor mix (10 µg each of pepstatin, chymostatin, and leupeptin per milliliter)] and then washed four times in wash buffer (lysis buffer without EGTA and Triton X-100). Recombinant Myt1 protein was eluted from the beads with 150 mM imidazole in wash buffer, frozen in liquid nitrogen, and stored at −80° C. A mock preparation was prepared in the same manner from uninfected Sf9 cells)] and centrifuged at 260,000 g for 1 hour. The membrane fraction was resuspended in three volumes of DB containing 500 mM NaCl and recentrifuged for 30 min. This salt-washed membrane was resuspended in three volumes of DB containing 0.5% Triton X-100, rotated for 20 min. and recentrifuged for 30 min. The resulting supernatant (the solubilized membrane fraction) was either frozen for later use or immediately subjected to immunodepletion. For this purpose, the solubilized membrane fraction was incubated with 20 µg of either anti-Myt1 or control antibodies per milliliter and bound to protein A beads as described (Rabbit antibodies to the COOH terminal-end of Myt1 (CNLLGMFDDATEQ) were affinity-purified. Affinity-purified rabbit antibodies to mouse immunoglobulin G (Cappel) served in control experiments. All other antibodies were described previously (A. Kumagai et al., *Mol.. Biol. Cell* 6, 199 (1995), Endogenous Myt1 was immunoprecipitated from Xenopus egg extracts with anti-Myt1 as described (P. R. Mueller et al., *Mol. Biol. Cell* 6, 119(1995) except that 0.5% Triton X-100 replaced NP-40). After this incubation, the beads were removed by centrifugation to yield Myt1-depleted or control-depleted supernatant. These depleted extracts were frozen in liquid nitrogen and stored at −80° C. The solubilized membrane fraction (lane 1), depleted supernatants (lanes 2 and 3), and isolated beads (lanes 4 and 5) were immunoblotted with anti-Myt1. Immpt., immunoprecipitate.

Figure 4B:
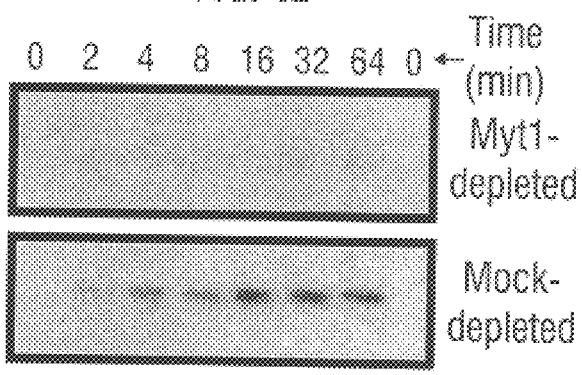
FIG. 4B is an immunoblot of reduced Cdc2-specific tyrosine kinase activity after removal of Myt1. These Myt1 - depleted or control extracts were incubated at 22° C. with a purified Cdc2-cyclin B1 complex in the presence of 2 mM ATP, 10 mM phosphocreatine, creatine kinase (100 $\mu$g/ml), 10 mM MgCl$_2$, and 1 mM vanadate. Samples were taken at the indicated times and immunoblotted with antibodies to phosphotyrosine.

FIG. 4B is an immunoblot of reduced Cdc2-specific tyrosine kinase activity after removal of Myt1. These Myt1-depleted or control extracts were incubated at 22° C. with a purified Cdc2-cyclin B1 complex in the presence of 2 mM ATP, 10 mM phosphocreatine, creatine kinase (100 µg/ml), 10 mM $MgCl_2$, and 1 mM vanadate. Samples were taken at the indicated times and immunoblotted with antibodies to phosphotyrosine.

The membrane fraction from Xenopus egg extracts possesses both $Thr^{14}$- and $Tyr^{15}$-specific kinase activities, whereas the cytosol fraction contains only the tyrosine-specific kinase. To determine whether Myt1 can account for a substantial portion of the Cdc2-specific inhibitory kinase activity found in Xenopus egg membranes, a series of immunodepletion studies were carried out with antibodies to the last 12 carboxyl residues of Myt1 (FIG. 4). Proteins from the detergent-solubilized membrane fraction from Xenopus eggs were immunoprecipitated with either anti-Myt1 or control antibodies. This immunodepletion with anti-Myt1 removed ~85% of the Myt1 protein (FIG. 4A). The Cdc2-specific kinase activities were measured in the Myt1-depleted or control extracts by adding a Cdc2-cyclin complex and then examining either the phosphotyrosine content of Cdc2 with antibodies to phosphocyrosine or the phosphorylation-dependent retardation of radiolabeled Cdc2 during gel electrophoresis. The tyrosine phosphorylation of Cdc2 was dramatically reduced in the Myt1-depleted extract (FIG. 4B). Similarly, using either $^{35}$S- or $^{32}$P-labeled Cdc2 as the substrate, the control extract shifted ~80% of the Cdc2 to its $Thr^{14}$-$Tyr^{15}$ doubly phosphorylated form, whereas the Myt1-depleted extract phosphorylated shifted only about 20% of the substrate (FIGS. 4, C and D).

Figure 4C:
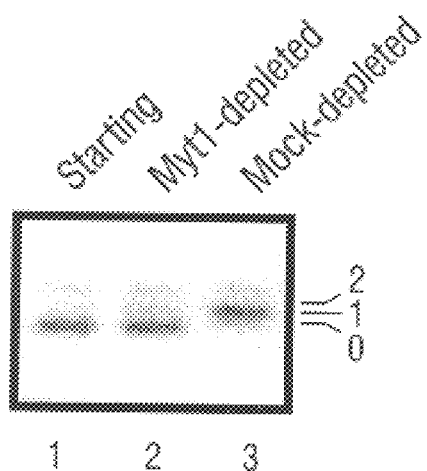
FIG. 4C is an immunoblot showing phosphorylation of Cdc2 and reduction of Cdc2-specific threonine and tyrosine kinase activities after removal of Myt1. The Myt1-depleted or control extracts were incubated as described in FIG. 4B except the Cdc2 subunit was labeled with $^{35}$S during its synthesis. After a 30-min incubation, samples were processed for autoradiography. In lane 1, the starting complex was loaded for reference. The phosphorylated forms of Cdc2 are indicated: 0, unshifted Cdc2; 1, partially shifted Cdc2 after phosphorylation on either Thr$^{14}$ or Tyr15; or 2, fully shifted Cdc2 after phosphorylation on both Thr$^{14}$ and Tyr$^{15}$.

FIG. 4C is an immunoblot showing phosphorylation of Cdc2 and reduction of Cdc2-specific threonine and tyrosine kinase activities after removal of Myt1. The Myt1 -depleted or control extracts were incubated as described in FIG. 4B except the Cdc2 subunit was labeled with 35S during its synthesis. After a 30-min incubation, samples were processed for autoradiography. In lane 1, the starting complex was loaded for reference. The phosphorylated forms of Cdc2 are indicated: 0, unshifted Cdc2; 1, partially shifted Cdc2 after phosphorylation on either $Thr^{14}$ or Tyr15;: or 2, fully shifted Cdc2 after phosphorylation on both $Thr^{14}$ and $Tyr^5$.

Figure 4D:
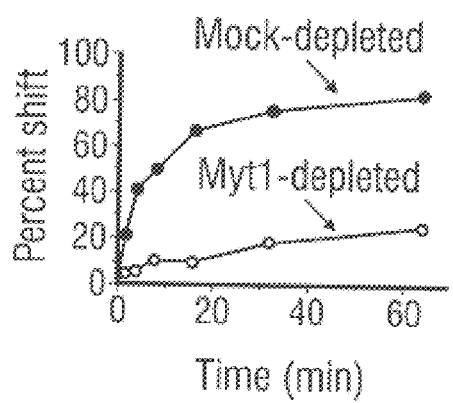
FIG. 4D shows a time course of experiment similar to (C), except that the Cdc2 was labeled with $^{32}$P on Thr$^{161}$before it was added to either the Myt1-depleted or control extracts as described in (B). At the indicated times, samples were processed for autoradiography. The graph shows the percentage of Cdc2 that is phosphorylated at both Thr$^{14}$ and Tyr$^{15}$.

FIG. 4D shows a time course of experiment similar to (C), except that the Cdc2 was labeled with $^{32}$P on $Thr^{161}$ before it was added to either the Myt1-depleted or control extracts as described in (B) At the indicated times, samples were processed for autoradiography. The graph shows the percentage of Cdc2 that is phosphorylated at both $Thr^{14}$ and $Tyr^{15}$.

The immunoprecipitated Myt1 protein efficiently phosphorylated Cdc2 in both assays. Taken together, these experiments suggest that Myt1 is a predominant Cdc2-specific inhibitory kinase in Xenopus egg membranes. Moreover, because all of the $Thr^{14}$-directed activity resides in the membrane fraction, Myt1 appears to be a major $Thr^{14}$-specific kinase in Xenopus eggs.

Example 3

Modification of Myt1 at M Phase

Figure 5A:
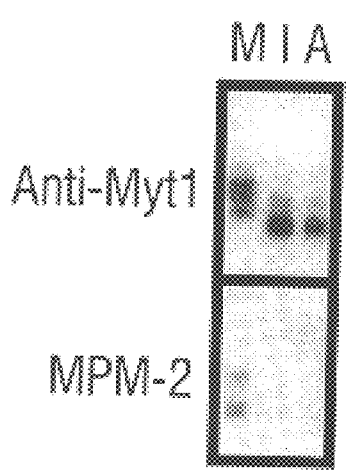
FIG. 5A is an immunoprecipitation of endogenous Myt1 from a cytostatic factor-arrested Xenopus egg extract (lane M), an interphase extract (lane 1), or an S phase-blocked extract that had been treated with aphidicolin (50 µg/ml) in the presence of sperm nuclei (1000 per microliter) (lane A). These samples were immunoblotted with anti-Myt1 (top panel) or monoclonal antibody MPM-2 (bottom panel).

The Wee1 kinase from Xenopus and humans is highly regulated during the cell cycle. In particular, Xenopus Wee1 is active during interphase but shows greatly reduced activity at mitosis as a result of extensive phosphorylation by two inhibitory kineses. To examine whether Myt1 is regulated during the cell cycle, endogenous Myt1 was immunoprecipitated from either M phase or interphase Xenopus egg extracts and measured its Cdc2-specific kinase activity. Two types of interphase extracts were prepared: one that was arrested in interphase with the replication inhibitor aphidicolin (M. Dasso et al., *Cell,* 61, 811 (1990) and another that contained no cell cycle inhibitor. Equivalent amounts of Myt1 protein were immunoprecipitated from the various extracts. However, the M phase form of Myt1 was clearly modified as indicated by a substantially reduced electrophoretic mobility (FIG. 5A). At least a portion of this modification appears to be phosphorylation, because the M phase, but not interphase, form of Myt1 reacts well with the mitotic phosphoprotein monoclonal antibody MPM-2 (FIG. 5A). This antibody specifically recognizes a phosphorylated epitope found on various mitotic proteins. Finally, the Cdc2-specific kinase activity of the various forms of Myt1 (FIG. 5B) was examined. The M phase form was about one-fifth as active as the Myt1 protein from either type of interphase extract.

FIG. 5A is an immunoprecipitation of endogenous Myt1 from a cytostatic factor-arrested Xenopus egg extract (lane M), an interphase extract (lane 1), or an S phase-blocked extract that had been treated with aphidicolin (50 µg/ml) in the presence of sperm nuclei (1000 per microliter) (lane A). These samples were immunoblotted with anti-Myt1 (top panel) or monoclonal antibody MPM-2 (bottom panel).

Figure 5B:
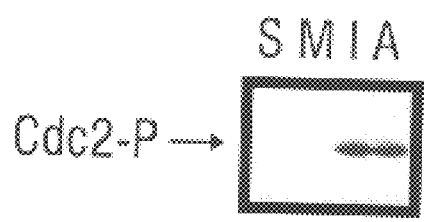
FIG. 5B is an immunoprecipitation of kinase activity of Myt1 measured as described in FIG. 2 with the N133A form of Cdc2 as the substrate (S). Lane S depicts a control assay without added Myt1 protein.

FIG. 5B is an immunoprecipitation of kinase activity of Myt1 measured as described in FIG. 2 with the N133A form of Cdc2 as the substrate (S). Lane S depicts a control assay without added Myt1 protein.

Moreover, like Xenopus Wee1, the activity of Myt1 was similar during interphase whether or not the replication checkpoint had been activated by aphidicolin. Similar results were obtained if either the TI4A or Y15F form of Cdc2 was used. These experiments indicate that Myt1 activity is substantially decreased at mitosis when Cdc2 must remain dephosphorylated on both $Thr^{14}$ and $Tyr^{15}$.

Although the invention has been described with reference to the presently preferred embodiment, it should be understood that various modifications can be made without departing from the spirit of the invention. Accordingly, the invention is limited only by the following claims.

What is claimed is:

1. An isolated Myt1 polypeptide comprising the amino acid sequence set forth in SEQ ID NO:2.

2. An isolated polypeptide comprising an amino acid sequence encoded by a nucleic acid sequence which hybridizes to the nucleic acid sequence set forth in SEQ ID NO:1 under highly stringent conditions, wherein the highly stringent conditions include 0.1×SSC at about 68° C. for 15 minutes, and wherein the polypeptide is a protein kinase.

3. The polypeptide of claim 2, wherein the polypeptide is a tyrosine protein kinase.

4. The polypeptide of claim 2, wherein the polypeptide is a threonine protein kinase.

5. The polypeptide of claim 2, wherein the polypeptide phosphorylates a Cdc-2 protein.

6. An isolated Myt1 polypeptide comprising a conservative variant of SEQ ID NO:2 or fragments thereof having kinase activity.

* * * * *

SEQUENCE LISTING

<160> NUMBER OF SEQ ID NOS: 9

<210> SEQ ID NO 1
<211> LENGTH: 2192
<212> TYPE: DNA
<213> ORGANISM: Xenopus sp.
<220> FEATURE:
<221> NAME/KEY: CDS
<222> LOCATION: (169)..(1812)

<400> SEQUENCE: 1

```
agtcatagaa gggactcggg gagtcggtgt gtgggaatgt gacggagatg cgcaaacggg     60
cgggtgttgt tgaagaggcg ttgggggccc aaatccagaa ttgtccttct gtatatctgg   120
agataaaaag gaccaccatt acgttcacct ttaaggtgcc tgctcatt atg cct gtt    177
                                                    Met Pro Val
                                                      1 cca ggg gat gac atg gga gag act ccc ctg act cgc act cca atc cct    225
Pro Gly Asp Asp Met Gly Glu Thr Pro Leu Thr Arg Thr Pro Ile Pro
        5                  10                  15 atg cct gct tac ttt agc cag gca gag caa agc ttt tca ctt aag aaa    273
Met Pro Ala Tyr Phe Ser Gln Ala Glu Gln Ser Phe Ser Leu Lys Lys
 20                  25                  30                  35 aga ggg cgc tct ctt tgc tat acc ctc cca ccc aga cct cca gtt aaa    321
Arg Gly Arg Ser Leu Cys Tyr Thr Leu Pro Pro Arg Pro Pro Val Lys
                 40                  45                  50 agc gct cta cct gta agc cgt atc ttc cca aat aaa cag cga tct tgg    369
Ser Ala Leu Pro Val Ser Arg Ile Phe Pro Asn Lys Gln Arg Ser Trp
             55                  60                  65 agc cag ccc aga cca cag agc gtt tct ttt cga agt ccc caa aat aaa    417
Ser Gln Pro Arg Pro Gln Ser Val Ser Phe Arg Ser Pro Gln Asn Lys
         70                  75                  80 acc cct gca agc aag ctt tat gac cag agc aaa gga gat aca ttt ttc    465
Thr Pro Ala Ser Lys Leu Tyr Asp Gln Ser Lys Gly Asp Thr Phe Phe
     85                  90                  95 aag cag tgt ttt aaa agc att tgc aaa tta gga aga gga tcc ttt ggg    513
Lys Gln Cys Phe Lys Ser Ile Cys Lys Leu Gly Arg Gly Ser Phe Gly
100                 105                 110                 115 gag gta tac aag gtg caa agc ctt gag gat gga tgc ttc tat gct gta    561
Glu Val Tyr Lys Val Gln Ser Leu Glu Asp Gly Cys Phe Tyr Ala Val
                120                 125                 130 aag cgt tct gta tct ccg ttc cgc ggt gag tca gac cgg caa cgg aag    609
Lys Arg Ser Val Ser Pro Phe Arg Gly Glu Ser Asp Arg Gln Arg Lys
            135                 140                 145 ctt cag gag gtg agg aag cat gag cga gtt ggg gag cac ccc aat tgc    657
Leu Gln Glu Val Arg Lys His Glu Arg Val Gly Glu His Pro Asn Cys
        150                 155                 160 cta cgt ttt gtg cga gca tgg gaa gag aaa cga atg ctc tac ctt cag    705
Leu Arg Phe Val Arg Ala Trp Glu Glu Lys Arg Met Leu Tyr Leu Gln
165                 170                 175 aca gag tta tgt gca ggg agt ttg caa cag cat tct gaa gaa ttt gct    753
Thr Glu Leu Cys Ala Gly Ser Leu Gln Gln His Ser Glu Glu Phe Ala
180                 185                 190                 195 ggg tct ctt cct cca cgt cga gta tgg aac ata act tgt gac ctg ctg    801
Gly Ser Leu Pro Pro Arg Arg Val Trp Asn Ile Thr Cys Asp Leu Leu
                200                 205                 210 cat ggt ctc aaa cat ctt cat gat cgc aac ctt ctg cac ctt gac att    849
His Gly Leu Lys His Leu His Asp Arg Asn Leu Leu His Leu Asp Ile
            215                 220                 225
```

```
aag cca gct aat gtc ttc att tct ttt tct ggt gtt tgc aaa ctt ggt        897
Lys Pro Ala Asn Val Phe Ile Ser Phe Ser Gly Val Cys Lys Leu Gly
        230                 235                 240 gat ttc gga ctc atg gta gaa ttg gat ggg act gaa gga agt ggg gaa        945
Asp Phe Gly Leu Met Val Glu Leu Asp Gly Thr Glu Gly Ser Gly Glu
    245                 250                 255 gca cag gaa ggt gac cct cgc tat atg gca cct gaa ctg ttg gat ggt        993
Ala Gln Glu Gly Asp Pro Arg Tyr Met Ala Pro Glu Leu Leu Asp Gly
260                 265                 270                 275 atc ttt tcg aag gct gct gat gtg ttc agt ctt gga atg agt ctt cta       1041
Ile Phe Ser Lys Ala Ala Asp Val Phe Ser Leu Gly Met Ser Leu Leu
                280                 285                 290 gaa gtc gct tgc aat atg gag ctt ccg aaa ggt gga gat ggt tgg caa       1089
Glu Val Ala Cys Asn Met Glu Leu Pro Lys Gly Gly Asp Gly Trp Gln
            295                 300                 305 cag ctg aga caa ggg cat ctc cct aca gag ttt aca tca gac ctg cca       1137
Gln Leu Arg Gln Gly His Leu Pro Thr Glu Phe Thr Ser Asp Leu Pro
        310                 315                 320 cca gat ttc cta aaa gtt ctt tct gca atg ctg gag cct gat tac cgc       1185
Pro Asp Phe Leu Lys Val Leu Ser Ala Met Leu Glu Pro Asp Tyr Arg
    325                 330                 335 cgc cgt gcc aca gta gac tgg cta ctc tcc ctt cct gct atc cgt aat       1233
Arg Arg Ala Thr Val Asp Trp Leu Leu Ser Leu Pro Ala Ile Arg Asn
340                 345                 350                 355 gca gag aga tgg agg atg gtg aca cta gcg cag gaa agg aca ctt ggc       1281
Ala Glu Arg Trp Arg Met Val Thr Leu Ala Gln Glu Arg Thr Leu Gly
                360                 365                 370 aag ata ata gca gtc tat cag ttc ata gtt tgg ctt cta tct ttc gtg       1329
Lys Ile Ile Ala Val Tyr Gln Phe Ile Val Trp Leu Leu Ser Phe Val
            375                 380                 385 ttt caa tgg cta aat cgt cct gtt ata gga ttt tta cat tac tgt gga       1377
Phe Gln Trp Leu Asn Arg Pro Val Ile Gly Phe Leu His Tyr Cys Gly
        390                 395                 400 ttg agg gct ctt cca agg tca cct ccc tgt tct cct ttt cct aac cat       1425
Leu Arg Ala Leu Pro Arg Ser Pro Pro Cys Ser Pro Phe Pro Asn His
    405                 410                 415 ctt ggg gag agc agc ttc tct agt gac tgg gat gat gag agt ctt ggt       1473
Leu Gly Glu Ser Ser Phe Ser Ser Asp Trp Asp Asp Glu Ser Leu Gly
420                 425                 430                 435 gat gat gtg ttt gag gta ccg cca agc cca ctg gcc act cac cga aat       1521
Asp Asp Val Phe Glu Val Pro Pro Ser Pro Leu Ala Thr His Arg Asn
                440                 445                 450 ctg aca tac cat ggg cag gag ctc att ggc aga cat tct cca gat cta       1569
Leu Thr Tyr His Gly Gln Glu Leu Ile Gly Arg His Ser Pro Asp Leu
            455                 460                 465 ctc tca agg ccg tca ctt gga agt acc tct acc cct cgc aat ttg tct       1617
Leu Ser Arg Pro Ser Leu Gly Ser Thr Ser Thr Pro Arg Asn Leu Ser
        470                 475                 480 cct gaa ttc agc atg aga aag agg tct gcc ctg cct cta acg cct aat       1665
Pro Glu Phe Ser Met Arg Lys Arg Ser Ala Leu Pro Leu Thr Pro Asn
    485                 490                 495 gtc agt cgg att agc cag gat tct aca ggc aag tct aga agc ccc tcc       1713
Val Ser Arg Ile Ser Gln Asp Ser Thr Gly Lys Ser Arg Ser Pro Ser
500                 505                 510                 515 acc agt cat agc tcc tct gga ttt gtg gat gct gaa gtc cag cgt acc       1761
Thr Ser His Ser Ser Ser Gly Phe Val Asp Ala Glu Val Gln Arg Thr
                520                 525                 530 tta ttt ctt cct cgc aat ctg ctc ggt atg ttt gac gat gcc acc gag       1809
Leu Phe Leu Pro Arg Asn Leu Leu Gly Met Phe Asp Asp Ala Thr Glu
            535                 540                 545
```

-continued

```
caa tgatagcagt gcagagtacc acacagcacc agacttttta ttttcaatc    1862
Gln aggtgatctt taacgccaac cattggccta tggcattgac ctgttggcat atgaaagtga  1922
aattgagagg tctacaacat attggatgta ttgagacaat ggctatttat acaatgcaca  1982
ttcagctgtg aaaaattaca cccgatatct gcatattcgc aaaagaaaat ggatgttgta  2042
taaaaatggt gactgggtta tggataatat aataggtgtg ttttttcatga tatcgccatg  2102 attaccgcta acatttctat aacttaagtt ttcagttctt gtttaaagtg tgtgtgtatt  2162
tatatttata taaaaacatt ttttttggga                                    2192
```

<210> SEQ ID NO 2
<211> LENGTH: 548
<212> TYPE: PRT
<213> ORGANISM: Xenopus sp.

<400> SEQUENCE: 2

```
Met Pro Val Pro Gly Asp Asp Met Gly Glu Thr Pro Leu Thr Arg Thr
  1               5                  10                  15

Pro Ile Pro Met Pro Ala Tyr Phe Ser Gln Ala Glu Gln Ser Phe Ser
             20                  25                  30

Leu Lys Lys Arg Gly Arg Ser Leu Cys Tyr Thr Leu Pro Pro Arg Pro
         35                  40                  45

Pro Val Lys Ser Ala Leu Pro Val Ser Arg Ile Phe Pro Asn Lys Gln
     50                  55                  60

Arg Ser Trp Ser Gln Pro Arg Pro Gln Ser Val Ser Phe Arg Ser Pro
 65                  70                  75                  80

Gln Asn Lys Thr Pro Ala Ser Lys Leu Tyr Asp Gln Ser Lys Gly Asp
                 85                  90                  95

Thr Phe Phe Lys Gln Cys Phe Lys Ser Ile Cys Lys Leu Gly Arg Gly
            100                 105                 110

Ser Phe Gly Glu Val Tyr Lys Val Gln Ser Leu Glu Asp Gly Cys Phe
        115                 120                 125

Tyr Ala Val Lys Arg Ser Val Ser Pro Phe Arg Gly Glu Ser Asp Arg
    130                 135                 140

Gln Arg Lys Leu Gln Glu Val Arg Lys His Glu Arg Val Gly Glu His
145                 150                 155                 160

Pro Asn Cys Leu Arg Phe Val Arg Ala Trp Glu Glu Lys Arg Met Leu
                165                 170                 175

Tyr Leu Gln Thr Glu Leu Cys Ala Gly Ser Leu Gln Gln His Ser Glu
            180                 185                 190

Glu Phe Ala Gly Ser Leu Pro Pro Arg Arg Val Trp Asn Ile Thr Cys
        195                 200                 205

Asp Leu Leu His Gly Leu Lys His Leu His Asp Arg Asn Leu Leu His
    210                 215                 220

Leu Asp Ile Lys Pro Ala Asn Val Phe Ile Ser Phe Ser Gly Val Cys
225                 230                 235                 240

Lys Leu Gly Asp Phe Gly Leu Met Val Glu Leu Asp Gly Thr Glu Gly
                245                 250                 255

Ser Gly Glu Ala Gln Glu Gly Asp Pro Arg Tyr Met Ala Pro Glu Leu
            260                 265                 270

Leu Asp Gly Ile Phe Ser Lys Ala Ala Asp Val Phe Ser Leu Gly Met
        275                 280                 285

Ser Leu Leu Glu Val Ala Cys Asn Met Glu Leu Pro Lys Gly Gly Asp
```

-continued

```
                    290                 295                 300
Gly Trp Gln Gln Leu Arg Gln Gly His Leu Pro Thr Glu Phe Thr Ser
305                 310                 315                 320

Asp Leu Pro Pro Asp Phe Leu Lys Val Leu Ser Ala Met Leu Glu Pro
                325                 330                 335

Asp Tyr Arg Arg Arg Ala Thr Val Asp Trp Leu Leu Ser Leu Pro Ala
            340                 345                 350

Ile Arg Asn Ala Glu Arg Trp Arg Met Val Thr Leu Ala Gln Glu Arg
        355                 360                 365

Thr Leu Gly Lys Ile Ile Ala Val Tyr Gln Phe Ile Val Trp Leu Leu
    370                 375                 380

Ser Phe Val Phe Gln Trp Leu Asn Arg Pro Val Ile Gly Phe Leu His
385                 390                 395                 400

Tyr Cys Gly Leu Arg Ala Leu Pro Arg Ser Pro Cys Ser Pro Phe
                405                 410                 415

Pro Asn His Leu Gly Glu Ser Ser Phe Ser Ser Asp Trp Asp Asp Glu
                420                 425                 430

Ser Leu Gly Asp Asp Val Phe Glu Val Pro Pro Ser Pro Leu Ala Thr
            435                 440                 445

His Arg Asn Leu Thr Tyr His Gly Gln Glu Leu Ile Gly Arg His Ser
        450                 455                 460

Pro Asp Leu Leu Ser Arg Pro Ser Leu Gly Ser Thr Ser Thr Pro Arg
465                 470                 475                 480

Asn Leu Ser Pro Glu Phe Ser Met Arg Lys Arg Ser Ala Leu Pro Leu
                485                 490                 495

Thr Pro Asn Val Ser Arg Ile Ser Gln Asp Ser Thr Gly Lys Ser Arg
            500                 505                 510

Ser Pro Ser Thr Ser His Ser Ser Gly Phe Val Asp Ala Glu Val
        515                 520                 525

Gln Arg Thr Leu Phe Leu Pro Arg Asn Leu Leu Gly Met Phe Asp Asp
    530                 535                 540

Ala Thr Glu Gln
545
```

```
<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:
      oligonucleotide for pcr of Myt1 nucleic acid
      sequence.
<220> FEATURE:
<221> NAME/KEY: modified_base
<222> LOCATION: (15)
<223> OTHER INFORMATION: i or C
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i
<220> FEATURE:
<221> NAME/KEY: modified_base
<222> LOCATION: (26)
<223> OTHER INFORMATION: i  or C

<400> SEQUENCE: 3
cggggtaccy traanhtngg ngaytngg                                     28
```

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide for PCR of Myt1.
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (17)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (21)
<223> OTHER INFORMATION: i
<220> FEATURE:
<221> NAME/KEY: modified_base
<222> LOCATION: (27)
<223> OTHER INFORMATION: i or C
<220> FEATURE:
<221> NAME/KEY: modified_base
<222> LOCATION: (30)
<223> OTHER INFORMATION: i or C

<400> SEQUENCE: 4
tcccccgggt gccanbnnws nccrttnybn gg                          32

<210> SEQ ID NO 5
<211> LENGTH: 13
<212> TYPE: PRT
<213> ORGANISM: Xenopus sp.

<400> SEQUENCE: 5

Cys Asn Leu Leu Gly Met Phe Asp Asp Ala Thr Glu Gln
 1               5                  10

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide for PCR.

<400> SEQUENCE: 6
cggcatatgc ctgttccagg ggatg                                  25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide for pcr.

<400> SEQUENCE: 7
caaggctttg caccttgtat acctc                                  25

<210> SEQ ID NO 8
<211> LENGTH: 222
<212> TYPE: PRT

<213> ORGANISM: Schizosaccharomyces pombe

<400> SEQUENCE: 8

```
Ser His Leu Leu Thr Arg Phe Arg Asn Val Thr Leu Leu Gly Ser Gly
  1               5                  10                  15
Glu Phe Ser Glu Val Phe Gln Val Glu Asp Pro Val Glu Lys Thr Leu
             20                  25                  30
Lys Tyr Ala Val Lys Lys Leu Lys Val Lys Phe Ser Gly Pro Lys Glu
         35                  40                  45
Arg Asn Arg Leu Leu Gln Glu Val Ser Ile Gln Arg Ala Leu Lys Gly
     50                  55                  60
His Asp His Ile Val Glu Leu Met Asp Ser Trp Glu His Gly Gly Phe
 65                  70                  75                  80
Leu Tyr Met Gln Val Glu Leu Cys Glu Asn Gly Ser Leu Asp Arg Phe
                 85                  90                  95
Leu Glu Glu Gln Gly Gln Leu Ser Arg Leu Asp Glu Phe Arg Val Trp
            100                 105                 110
Lys Ile Leu Val Glu Val Ala Leu Gly Leu Gln Phe Ile His His Lys
        115                 120                 125
Asn Tyr Val His Leu Asp Leu Lys Pro Ala Asn Val Met Ile Thr Phe
    130                 135                 140
Glu Gly Thr Leu Lys Ile Gly Asp Phe Gly Met Ala Ser Val Trp Pro
145                 150                 155                 160
Val Pro Arg Gly Met Glu Arg Glu Gly Asp Cys Glu Tyr Ile Ala Pro
                165                 170                 175
Glu Val Leu Ala Asn His Leu Tyr Asp Lys Pro Ala Asp Ile Phe Ser
            180                 185                 190
Leu Gly Ile Thr Val Phe Glu Ala Ala Ala Asn Ile Val Leu Pro Asp
        195                 200                 205
Asn Gly Gln Ser Trp Gln Lys Leu Arg Ser Gly Asp Leu Ser
    210                 215                 220
```

<210> SEQ ID NO 9
<211> LENGTH: 240
<212> TYPE: PRT
<213> ORGANISM: Xenopus sp.

<400> SEQUENCE: 9

```
Ser Arg Tyr Lys Thr Glu Phe Leu Glu Ile Glu Lys Ile Gly Ala Gly
  1               5                  10                  15
Glu Phe Gly Ser Val Phe Lys Cys Val Lys Arg Leu Asp Gly Cys Phe
             20                  25                  30
Tyr Ala Ile Lys Arg Ser Lys Lys Pro Leu Ala Gly Ser Thr Asp Glu
         35                  40                  45
Gln Leu Ala Leu Arg Glu Val Tyr Ala His Ala Val Leu Gly His His
     50                  55                  60
Pro His Val Val Arg Tyr Tyr Ser Ala Trp Ala Glu Asp Asp His Met
 65                  70                  75                  80
Ile Ile Gln Asn Glu Tyr Cys Asn Gly Gly Ser Leu Gln Asp Leu Ile
                 85                  90                  95
Val Asp Asn Asn Lys Glu Gly Gln Phe Val Leu Glu Gln Glu Leu Lys
            100                 105                 110
Glu Ile Leu Leu Gln Val Ser Met Gly Leu Lys Tyr Ile His Gly Ser
        115                 120                 125
Gly Leu Val His Met Asp Ile Lys Pro Ser Asn Ile Phe Ile Cys Arg
```

-continued

```
                130                 135                 140
Lys Gln Thr Glu Leu Gly Gln Glu Glu Ser Asp Gly Glu Asp Asp Leu
145                 150                 155                 160

Ser Ser Gly Ser Val Leu Tyr Lys Ile Gly Asp Leu Gly His Val Thr
                165                 170                 175

Ser Ile Leu Asn Pro Gln Val Glu Glu Gly Asp Ser Arg Phe Leu Ala
                180                 185                 190

Asn Glu Ile Leu Gln Glu Asp Tyr Ser Gln Leu Pro Lys Ala Asp Ile
                195                 200                 205

Phe Ala Leu Gly Leu Thr Ile Ala Leu Ala Ala Gly Ala Ala Pro Leu
                210                 215                 220

Pro Cys Asn Glu Asp Ser Trp His His Ile Arg Lys Gly Asn Leu Pro
225                 230                 235                 240
```